US 8,178,098 B2

(12) United States Patent
Lahn et al.

(10) Patent No.: US 8,178,098 B2
(45) Date of Patent: May 15, 2012

(54) METHOD TO INHIBIT AIRWAY HYPERRESPONSIVENESS USING AEROSOLIZED T CELL RECEPTOR ANTIBODIES

(75) Inventors: Michael F. Lahn, Zionsville, IN (US); Willi K. Born, Denver, CO (US); Arihiko Kanehiro, Okayama (JP); Erwin Gelfand, Englewood, CO (US)

(73) Assignee: National Jewish Health, Denver, CO (US)

( * ) Notice: Subject to any disclaimer, the term of this patent is extended or adjusted under 35 U.S.C. 154(b) by 1422 days.

(21) Appl. No.: 09/826,319

(22) Filed: Apr. 3, 2001

(65) Prior Publication Data

US 2002/0172677 A1 Nov. 21, 2002

(51) Int. Cl.
*A61K 39/395* (2006.01)
*C07K 16/28* (2006.01)

(52) U.S. Cl. ............... 424/144.1; 424/154.1; 424/173.1; 424/810; 530/388.75; 530/388.22; 530/389.6; 530/868

(58) Field of Classification Search ............... 424/144.1, 424/154.1, 173.1, 143.1, 133.1, 810; 530/387.3, 530/388.22, 388.75, 384.6, 868
See application file for complete search history.

(56) References Cited

U.S. PATENT DOCUMENTS

| 5,185,250 A | 2/1993 | Brenner et al. ............... 435/69.3 |
| 5,223,426 A | 6/1993 | Skibbens et al. ......... 435/240.27 |
| 5,869,448 A * | 2/1999 | Arrhenius et al. ............... 514/11 |
| 5,871,734 A | 2/1999 | Lobb et al. ................. 424/144.1 |
| 5,958,410 A * | 9/1999 | Wigzell et al. ............. 424/144.1 |
| 6,054,292 A | 4/2000 | Hillman et al. ............... 435/69.1 |
| 6,113,901 A | 9/2000 | Bluestone .................. 424/154.1 |
| 6,165,463 A | 12/2000 | Platz et al. .................. 424/130.1 |
| 6,171,799 B1 | 1/2001 | Skibbens et al. ............... 435/7.1 |
| 2002/0037286 A1 * | 3/2002 | Krause et al. ............. 424/155.1 |

FOREIGN PATENT DOCUMENTS

WO    WO 01/22816    4/2001

OTHER PUBLICATIONS

Sato et al., J. Immunol. 155:2938-2947.*
Schram et al., *Amer. J. Respir. Cell Mol. Biol.*, 22(2):218-25 (2000): Abstract.
Fahy et al., *Am. J. Respir. Crit. Care Med.*, 160(3):1023-1027 (1999).
Hamelmann et al., *J. Exp. Med.*, 183:1719-1729 (1996).
Holt, *J. Exp. Med.*, 183:1297-1301 (1996).
Huber et al., *J. Immunol.*, 165:4174-4181 (2000).
Kon et al., *Lancet*, 352:1109-13 (1998).
Kon et al., *Inflamm. Res.*, 48:516-523 (1999).
Lahn et al., *Nature Medicine*, 5(10):1150-1156 (1999).
Milgrom et al., *N. Engl. J. Med.*, 341:1966-1973 (1999).
Offner et al., *Springer Semin Immunopathol*, 21:77-90 (1999).
Seymour et al., *J. Exp. Med.*, 187(5):721-731 (1998).
Takeda et al., *J. Exp. Med.*, 186(3):449-454 (1997).
Yocum, *Semin Arthritis Rheum*, 29:27-35 (1999).

* cited by examiner

*Primary Examiner* — Ronald Schwadron
(74) *Attorney, Agent, or Firm* — Sheridan Ross P.C.

(57) ABSTRACT

Disclosed is a method to reduce airway hyperresponsiveness in an animal by the direct delivery to the lungs of aerosolized antibodies against T cell receptors. The method is particularly useful for treating airway hyperresponsiveness associated with allergic inflammation, is effective at extremely low doses of antibody, and does not have a substantial effect on the peripheral immune system.

4 Claims, 4 Drawing Sheets

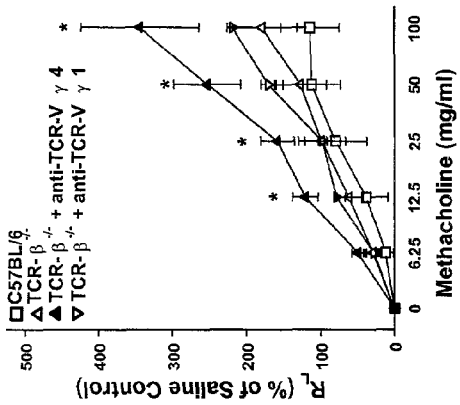
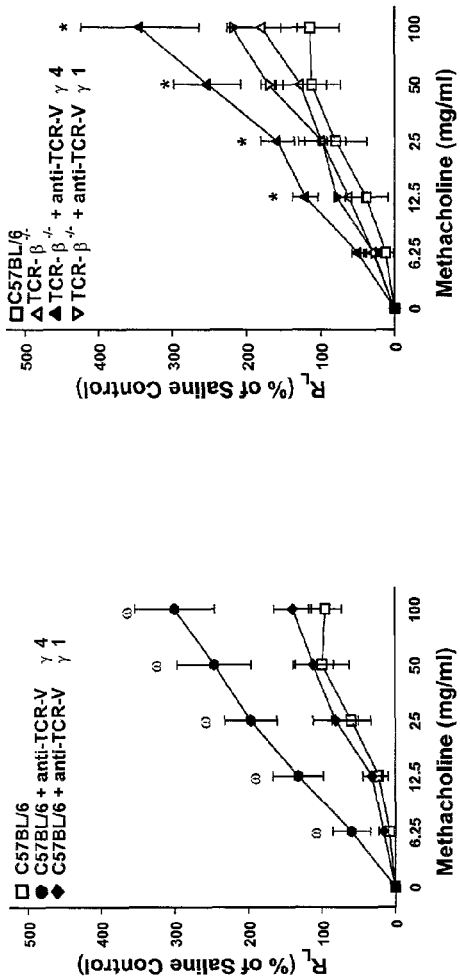
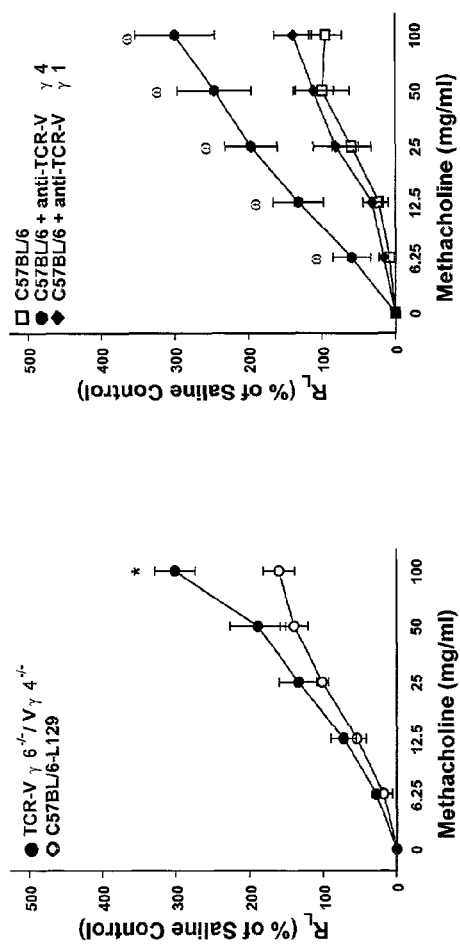
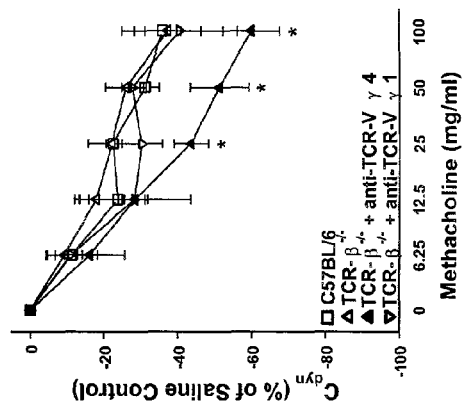
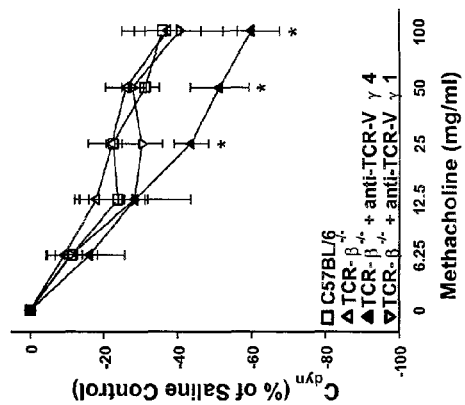
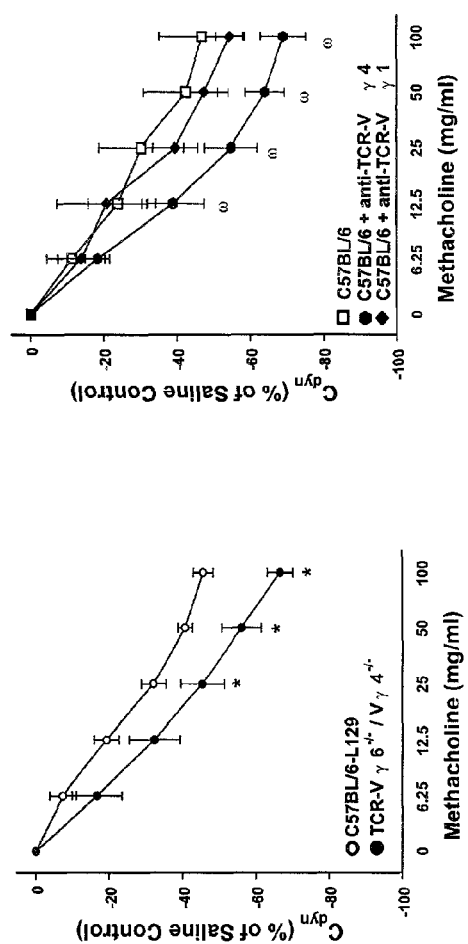

METHOD TO INHIBIT AIRWAY HYPERRESPONSIVENESS USING AEROSOLIZED T CELL RECEPTOR ANTIBODIES

GOVERNMENT RIGHTS

This invention was supported, in part, by Grant Nos. R01 HL-65410; AI-40611; HL-36557; HL-61005; and R01 AI-44920, all awarded by the National Institutes of Health, and Grant No. R825702, awarded by the Environmental Protection Agency. The government has certain rights to this invention.

FIELD OF THE INVENTION

This invention generally relates to the use of aerosolized antibodies against T cell receptors for the inhibition of airway hyperresponsiveness (AHR). Specifically, aerosolized antibodies against receptors on both $\alpha\beta$ and $\gamma\delta$ T cells are disclosed for the treatment of AHR.

BACKGROUND OF THE INVENTION

A variety of inflammatory agents can provoke airflow limitation, including allergens, cold air, exercise, infections and air pollution. In particular, allergens and other agents in allergic or sensitized mammals (i.e., antigens and haptens) cause the release of inflammatory mediators that recruit cells involved in inflammation. Such cells include lymphocytes, eosinophils, mast cells, basophils, neutrophils, macrophages, monocytes, fibroblasts and platelets. A common consequence of inflammation is airway hyperresponsiveness (AHR). A variety of studies have linked the degree, severity and timing of the inflammatory process with the degree of airway hyperresponsiveness.

Airway hyperresponsiveness (AHR) is the result of complex pathophysiological changes in the airway. A variety of studies have linked the degree, severity and timing of the inflammatory process with the degree of airway hyperresponsiveness. However, the mechanisms leading to AHR are still poorly understood and can be attributed to both immune-dependent and immune-independent mechanisms. Essentially all of the T cell-mediated effects described so far are in the former category. However, T cells from hyperresponsive mice can increase baseline airway tone in hyporesponsive mice after cell transfer.

Currently, therapy for treatment of inflammatory diseases involving AHR, such as moderate to severe asthma and chronic obstructive pulmonary disease, predominantly involves the use of glucocorticosteroids and other anti-inflammatory agents. These agents, however, have the potential of serious side effect, including, but not limited to, increased susceptibility to infection, liver toxicity, drug-induced lung disease, and bone marrow suppression. Thus, such drugs are limited in their clinical use for the treatment of lung diseases associated with airway hyperresponsiveness. The use of anti-inflammatory and symptomatic relief reagents is a serious problem because of their side effects or their failure to attack the underlying cause of an inflammatory response. There is a continuing requirement for less harmful and more effective reagents for treating inflammation. Thus, there remains a need for processes using reagents with lower side effect profiles, less toxicity and more specificity for the underlying cause of AHR.

Airway hyperresponsiveness in asthma and other conditions associated with allergic inflammation increases after exposure to allergen. The level of responsiveness can be demonstrated by showing increased responses to bronchoconstrictors such as methacholine (MCh). This heightened responsiveness is thought to result from a complex inflammatory cascade involving several cell types, including T lymphocytes and eosinophils (Gelfand & Irvin, (1997) *Nat. Med.* 3, 382-384; Wills-Karp, (1999) *Ann. Rev. Immunol.* 17, 255-281). T lymphocytes exert many of their effects by secreting an array of cytokines. More specifically, the present inventors and others have previously shown that $\alpha\beta$ T cells are necessary for the development of allergic inflammation and airway hyperresponsiveness (AHR) (e.g., (Hamelmann et al., (1996) *J. Exp. Med.* 183:1719-1729; Holt, (1996) *J. Exp. Med.* 183: 1297-1301; Takeda et al. (1997) *J. Exp. Med.* 186:449-454; and Lahn et al., (1999) *Nature Med.* 5:1150-6). In addition, it has been shown that in a model of acute allergic inflammation TCR-$\beta^{-/-}$ mice do not develop eosinophilia in the BAL fluid and in the lung tissue and do not develop AHR. (Lahn et al., (1999) ibid.) and similar results were shown in a chronic model of allergic inflammation (Seymour et al. (1998) *J. Exp. Med.* 187:721-731).

In recent years humanized monoclonal antibodies (mAb) have become an attractive pharmacological treatment option in patients suffering from different diseases (See, e.g., Table 1). Several publications and patents describe antibodies against various receptors on T cells, including the T cell antigen receptor (TCR), CD3, and CD4. For example, U.S. Pat. Nos. 4,658,019 and 6,113,901 describe antibodies against the CD3 complex and the use of such antibodies in the suppression of the immune system ('019), or the induction of passive immunity ('901). U.S. Pat. Nos. 5,223,426 and 6,171,799 describe antibodies against the TCR $\alpha$ or $\beta$ chains and the use of such antibodies to treat conditions and disorders of the immune system by stimulation or suppression of T cells. Among the application of mAbs as immunotherapeutics, the use of mAbs against CD3 complex, CD4 and IL-2R have been studied in different clinical trials (Yocum, Seminars in *Arthritis and Rheumatism* 29:27-35 (1999); Offner et al., *Springer Seminars in Immunopathology* 21:77-90 (1999)). In lung related diseases, however, only mABS against CD4 and IgE have been used in patients with asthma (Kon et al., *Lancet* 352:1109-13 (1998); Kon et al., *Inflammation Research* 48:516-23 (1999); Milgrom et al., *N Engl J Med* 341:1966-73 (1999)). In both these therapeutic approaches, mAbs were applied intravenously.

TABLE 1

Currently Available Monoclonal Antibodies for Clinical Application

| Name | Action | Drug Name (Company) | Indication | Administration (Adults) |
|---|---|---|---|---|
| Palivizumab | IgG1k against A antigenic site of the F protein of RSV | Synagis (MedImmune) | RSV in children | 15 mg/kg i.m. |
| Basiliximab | IgG1K against IL-2R$\alpha$ (CD25) | Simulect (Novartis) | Organ rejection, Prophylaxis | 20 mg each (2 doses) |
| Daclizumab | IgG1 against $\alpha$-subunit (Tac subunit) of IL-2R | Zenapax (Roche) | Organ rejection, Prophylaxis | 1 mg/kg i.v. (5 doses) |

TABLE 1-continued

Currently Available Monoclonal Antibodies for Clinical Application

| Name | Action | Drug Name (Company) | Indication | Administration (Adults) |
|---|---|---|---|---|
| Muromonab-CD3 | IgG2a against T3 (CD3) | Orthoclone OKT3 (Ortho Biotech) | Organ rejection | 5 mg/day for 10-14 days as i.v. bolus |
| Etanercept | Dimeric fusion protein consisting of the extracellular ligand-binding portion of TNF-Rp75 | Enbrel (Immunex) | Rheumatoid Arthritis | 25 mg twice weekly s.c. |
| Rituximab | IgG1K against CD20 | Rituxan (IDEC/Genentech) | CD20+ Non-Hodgkin's Lymphoma | 375 mg/m$^2$ as i.v. infusion once weekly for 4 doses |
| Abiciximab | MAb against glycoprotein-IIb/IIIa-R on platlets (clone c7E3 Fab) | | Thrombembolus | |
| Trastuzumab | MAb against extracellular domain of hEGF-R2 protein (HER2) | Herceptin (Genentech) | HER2 overexpressing Breast Cancer | Initially, 4 mg/kg over 90 min, then 2 mg/kg over 30 min weekly |
| Edrecolomab | MAb (clone 17-1A) against colon tumor antigen 17-1A | Panorex (?) | Adjuvant therapy in colon cancer | 500 mg i.v., then monthly 100 mg |
| Keliximab | MAb against CD4 | (SmithKline Beecham) | RA, MS, IBD, Skin disorders, asthma | 0.5-1.5 mg/kg i.v. |
| huMAb-E25 | Mab against IgE | (Genentech) | Asthma | i.v. |
| Mab PM-81 and AML-2-23 | | (Medarex) | Exogenous depletion of CD14+ and CD15+ AML bone marrow cells from patients undergoing bone marrow transplantation | Experimental ? |
| MAb for immunization against lupus nephritis | | (VivoRx Autoimmune) | Lupus nephritis | Experimental ? |
| MAb PM-81 | | (Medarex) | Adjunctive treatment for AML | Experimental ? |
| MAb to CD22 (radiolabelled) | | LymphoCIDE (Immunomedics) | NHL | Experimental ? |
| MAb to CMV | | (Protein Design Labs) | CMV retinitis in AIDS | Experimental ? |
| MAb to h-HBV | | (Protein Design Labs) | Prophylaxis of Hepatitis B reinfection in liver transplantation | Experimental ? |
| MAb B43.13 | | OVArex Mab-B43.13 (AltaRex) | Epithelial Ovarian Cancer | Experimental ? |
| Nebacumab | IgM (clone HA-1A) binds to Lipid A | Centoxin (Centocor) | Gram-negative bacterimia progressed to septic shock | Experimental; withdrawn from European Market: 100 mg i.v. over 30 min |
| Edobacomab | IgM (clone ES) against core glycolipid | | Gram-negative bacterimia only | Experimental ? |
| MAb MSL-109 | antiviral | (Sandoz) | AIDS | Experimental, Phase I |
| Mab 5c8 | | (Biogen) | Immune Thrombocytopenic purpura, SLE | Experimental ? |

Recently, there has been some interest in delivery mechanisms for therapeutic antibodies. One area of interest is in the delivery of therapeutic antibodies by pulmonary delivery. For example, U.S. Pat. No. 6,165,463 to Inhale Therapeutic Systems, Inc. describes a dispersible dry powder that can be used for the pulmonary delivery of antibodies. The '463 patent references several different therapeutic antibodies that are currently being evaluated for use in the treatment of various conditions, including various viral infections, cancer, bacterial infections, allergic reactions and other inflammatory conditions, particularly those that affect the pulmonary tissues.

However, in practice, at least with regard to airway responses in the lung, attempts to use aerosolized therapeutic antibodies have not generally met with success. For example, Fahy et al. used aerosolized anti-IgE to test whether direct delivery of the antibody to the airway would have the same effect as the systemic delivery of the antibody, which attenuated early and late phase responses to inhaled allergen (Fahy et al., 1999, *Am. J. Respir. Crit. Care Med.* 160:1023-1027). It was shown that the aerosolized anti-IgE did not inhibit the airway responses to inhaled allergen and in at least one subject, the antibody proved to be immunogenic. Fahy et al. concluded that the observed lack of efficacy was probably due to the inability of the aerosol route of delivery to result in high enough concentrations of antibody in the lung tissue compartments to neutralize IgE. Indeed, U.S. Pat. No. 6,165,463, described above, indicates that antibodies are considered to be "low potency" drugs, and therefore indicates that fairly high concentrations of antibodies (e.g., in the milligram per milliliter range) should be formulated for aerosol delivery.

SUMMARY OF THE INVENTION

In difference to previously described clinical approaches for the treatment of diseases of the airways, the present inventors have used aerosolized antibodies against T cell receptors to modify diseases in the lung. The present inventors have shown that this method is highly effective at reducing airway hyperresponsiveness, targets pulmonary T cell populations in the absence of any substantial effect on peripheral T cells, and most surprisingly, the antibodies can be administered at extremely low doses which are believed to be at least about 1000-fold lower than systemic doses of antibody required to achieve the same effect. Therefore, the present inventors have discovered a novel method for treating immune related diseases in the lung without significantly affecting systemic immune responses of the host.

The present invention generally relates to a method to reduce airway hyperresponsiveness in a mammal that has, or is at risk of developing, airway hyperresponsiveness. The method includes the step of administering to the lungs of the mammal an aerosolized antibody formulation comprising antibodies that selectively bind to a receptor on a T cell. The receptor on the T cell can include, but is not limited to, an αβ T cell antigen receptor (αβ TCR), γδ T cell antigen receptor (γδ TCR), a murine TCR comprising Vγ1, a human TCR comprising Vγ9, a human TCR comprising Vδ1, CD4, CD8 and CD3. In one embodiment, the antibody selectively binds to the CD8 β chain. In another embodiment, the formulation includes antibodies of at least two different specificities, such as an antibody that selectively binds to an αβ T cell antigen receptor and an antibody that selectively binds to a γδ T cell antigen receptor. In one aspect, the antibody is a humanized monoclonal antibody. Preferably, the antibody does not stimulate T cell activation. In one aspect, the antibody is a monovalent antibody. In another aspect, the antibody is a neutralizing antibody. In a preferred embodiment, the mammal is a human.

In the method of the present invention, the aerosolized antibody formulation is preferably administered at a dose of less than about 500 µg antibody per milliliter of formulation, and more preferably, at a dose of less than about 250 µg antibody per milliliter of formulation, and more preferably, at a dose of less than about 100 µg antibody per milliliter of formulation, and more preferably, at a dose of less than about 50 µg antibody per milliliter of formulation, and even more preferably, at a dose of between about 5 µg antibody and about 10 µg antibody per milliliter of formulation.

In one embodiment, the antibody formulation is administered at a dose of less than about 400 µg×kilograms$^{-1}$ body weight of the mammal. In another embodiment, the antibody formulation is administered at a dose of less than about 40 µg×kilograms$^{-1}$ body weight of the mammal.

In one aspect, the aerosolized antibody formulation comprises less than 35% by weight of the antibody.

In one aspect, the aerosolized antibody formulation comprises a pharmaceutically acceptable carrier. The pharmaceutically acceptable carrier can include, but is not limited to: a dry, dispersible powder; small capsules; liposomes; and a nebulized spray. In one aspect, the aerosolized antibody formulation is administered to the mammal in conjunction with another agent that supports the treatment of AHR including, but not limited to: corticosteroids, (oral, inhaled and injected), β-agonists (long or short acting), leukotriene modifiers (inhibitors or receptor antagonists), antihistamines, phosphodiesterase inhibitors, sodium cromoglycate, nedocrimal, and theophylline.

In one embodiment, the mammal has been sensitized to an allergen and has been exposed to, or is at risk of being exposed to, an amount of the allergen that is sufficient to induce airway hyperresponsiveness (AHR) in the mammal in the absence of the aerosolized antibody formulation. Preferably, the aerosolized antibody formulation is administered within a time period of between 48 hours or less prior to exposure to an AHR provoking stimulus that is sufficient to induce AHR, and within 48 hours or less after the detection of the first symptoms of AHR. In one aspect, the aerosolized antibody formulation is administered upon the detection of the first symptoms of acute onset AHR. In another aspect, the aerosolized antibody formulation is administered within 1 hour after the detection of the first symptoms of acute onset AHR. In another aspect, the aerosolized antibody formulation is administered within 12 hours or less prior to exposure to a AHR provoking stimulus that is sufficient to induce acute onset AHR. In another aspect, the aerosolized antibody formulation is administered within 2 hours or less prior to exposure to a AHR provoking stimulus that is sufficient to induce acute onset AHR. In another aspect, the aerosolized antibody formulation reduces the airway hyperresponsiveness of the mammal such that the $FEV_1$ value of the mammal is improved by at least about 5%. Preferably, the administration of the aerosolized antibody formulation does not substantially affect peripheral immune function in the mammal.

BRIEF DESCRIPTION OF THE DRAWINGS OF THE INVENTION

FIGS. 4A and 4B show the airway resistance ($R_L$) (FIG. 4A) and dynamic compliance ($C_{dyn}$) (FIG. 4B) in TCR-Vγ4/6$^{-/-}$ mice using the suboptimal method of airway sensitization.

FIGS. 4C and 4D show the airway resistance ($R_L$) (FIG. 4C) and dynamic compliance ($C_{dyn}$) (FIG. 4D) in C57BL/6 mice treated with aerosolized anti-TCR-Vγ4 and anti-TCR-Vγ1, using the suboptimal method of airway sensitization.

FIGS. 4E and 4F show the airway resistance ($R_L$) (FIG. 4C) and dynamic compliance ($C_{dyn}$) (FIG. 4D) in TCR-β$^{-/-}$ mice treated with aerosolized anti-TCR-Vγ4 and anti-TCR-Vγ1, using the suboptimal method of airway sensitization.

DETAILED DESCRIPTION OF THE INVENTION

Figure 1A:
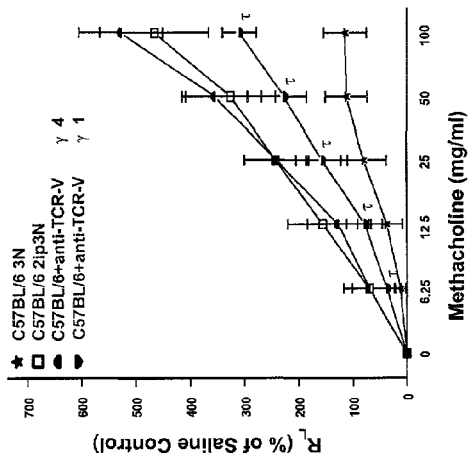
FIGS. 1A and 1B show the airway resistance ($R_L$) (FIG. 1A) and dynamic compliance ($C_{dyn}$) (FIG. 1B) for mice receiving anti-TCR-β by aerosol and intravenous delivery.
Figure 1C:
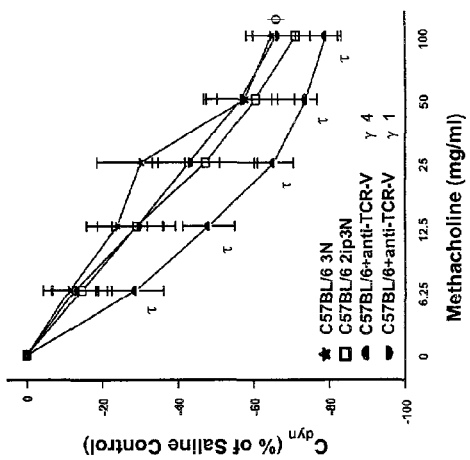
FIGS. 1C and 1D show the airway resistance ($R_L$) (FIG. 1C) and dynamic compliance ($C_{dyn}$) (FIG. 1D) for mice receiving anti-TCR-β by aerosol and intravenous delivery.

The present invention generally relates to a method to reduce or prevent airway hyperresponsiveness (AHR) in an animal that has, or is at risk of developing, airway hyperresponsiveness, by administering to the lungs of the animal an aerosolized antibody formulation comprising antibodies that selectively bind to a receptor on a T cell. Preferably, the animal has, or is at risk of developing, airway hyperresponsiveness associated with inflammation. For example, airway hyperresponsiveness is commonly associated with allergic inflammation and/or viral-induced inflammation. Airway hyperresponsiveness associated with allergic inflammation can occur in a patient that has, or is at risk of developing, a condition including, but not limited to, any chronic obstructive disease of the airways. Such conditions include, but are not limited to: asthma, chronic obstructive pulmonary disease, allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma and parasitic lung disease. Airway hyperresponsiveness associated with viral-induced inflammation can occur in a patient that has, or is at risk of developing, an infection by a virus including, but not limited to, respiratory syncytial virus (RSV), parainfluenza virus (PIV), rhinovirus (RV) and adenovirus. The present invention is also useful for the treatment of other diseases and conditions of the lung, including but not limited to, lung cancer and idiopathic pulmonary disease.

The present inventors have shown that the administration of aerosolized antibodies against receptors on T cells that cause the depletion or inactivation of the T cell is highly effective for reducing airway hyperresponsiveness in an animal, and particularly, in an animal that has airway hyperresponsiveness associated with allergic inflammation. The demonstration of the effectiveness of this protocol is both surprising and advantageous over other prior methods of treating allergic inflammation by systemic administration of antibodies against T cells and other methods of treating allergic airway disease by the administration of anti-IgE, including by aerosol delivery. First, in contrast to the aerosolized anti-IgE administration, described by Fahy et al. (1999, *Am. J. Respir. Crit. Care Med.* 160:1023-1027), the present inventors have demonstrated that this method is highly effective at reducing airway hyperresponsiveness. Indeed, in the art-accepted model of allergic inflammation and airway hyperresponsiveness, the present inventors have demonstrated that administration of aerosolized antibodies against T cell receptors significantly reduces airway hyperresponsiveness at a level that is at least as effective as systemic administration of the same antibody.

Second, the method targets pulmonary T cell populations in the absence of any substantial effect on peripheral T cells, which is a large advantage over previously described methods which target T cell responses systemically, since peripheral immune responses (i.e., immune responses outside the localized area of delivery, such as in the spleen or lymph nodes) are neither substantially stimulated nor substantially inhibited. By "substantially", it is meant that the response detected in the periphery, if any, is very small, and is typically less than about 10%, and preferably less than about 5%, and more preferably less than about 2%, and even more preferably less than about 1%, of the response that would be detected if the antibody was administered systemically.

Third, the present inventors provide evidence herein that targeting γδ T cells that have been recruited to the allergic site by the localization of the present method reduces allergic inflammation-associated exacerbation of AHR without affecting the adaptive immune system. Finally, and most surprisingly, in contrast to the evidence and assertions in both Fahy et al. and U.S. Pat. No. 6,165,463, as well as generally in the art, that antibodies delivered by aerosol must be administered in high doses to overcome the effects of expected low potency and to successfully reach the target airways, the method of the present invention is effective at extremely low doses of antibody. Indeed, the method of the present invention achieves efficacy with antibody doses that are believed to be about 1000-fold or more lower than systemic doses of antibody required to achieve the same effect.

The present invention specifically includes the administration directly to the lung of at least one aerosolized antibody in a formulation (i.e., an aerosolized antibody formulation). Accordingly, the method of the present invention includes the use of an antibody or antigen binding fragment that selectively binds to a receptor on a T cell which, by causing apoptosis of the T cell, otherwise targeting the T cell for depletion from the pulmonary tissues, or causing inhibition of T cell activity, reduces airway hyperresponsiveness in the patient. According to the present invention, the phrase "selectively binds to" refers to the ability of an antibody, antigen binding fragment or binding partner of the present invention to preferentially bind to specified proteins (e.g., a TCR). More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

As used herein, a "receptor on a T cell" generally refers to any receptor that is expressed by a T cell (i.e., a T lymphocyte). Such receptors include, but are not limited to, the T cell antigen receptor (also referred to herein as a TCR), including TCRs from both a and γδ T cells; the CD3 complex; CD4; and CD8. To be useful in the present invention, the binding of the receptor by an antibody must result in neutralization (depletion, removal) of the T cell. Therefore, preferred receptors to target using the present method are any receptors that, when bound by a depleting (e.g., neutralizing) antibody, cause the depletion or immobilization (e.g., apoptosis via complement activation, blockage, removal, or phagocytosis) of the T cell to which the antibody binds. Preferably, the antibodies used in the present invention do not stimulate the T cells. The receptors specifically mentioned above are particularly preferred receptors to target using antibodies according to the method of the present invention. A most preferred T cell receptor to target by the method of the present invention is the T cell antigen receptor (TCR).

An "αγ T cell" is a lineage of T lymphocytes found in mammalian species and birds that expresses an antigen receptor (i.e., a TCR) that includes an α chain and β chain. Similarly, a "γδ T cell" is a distinct lineage of T lymphocytes found in mammalian species and birds that expresses a particular antigen receptor (TCR) that includes a γ chain and a δ chain. The γ and δ chains are distinguished from the α and β chains that make up the TCR of the perhaps more commonly referenced αβ T cells. Both the αβ heterodimer of αβ T cells and the γδ heterodimer of γδ T cells are expressed on the surface of the respective T cell and are associated with the CD3 complex on the cell surface. The γ and δ chains of the γδ T cell receptor should not be confused with the γ and δ chains of the CD3 complex. According to the present invention, the terms "T lymphocyte" and "T cell" can be used interchangeably.

In one embodiment, the method for regulation of airway hyperresponsiveness of the present invention is directed to the depletion of γδ T cells that are identified as being particularly relevant during the acute onset of AHR in an animal. In one aspect, a preferred γδ T cell for which inhibition is believed to be particularly effective for reducing AHR has a T cell receptor (TCR) that comprises the equivalent of the murine Vγ1 chain (i.e., the variable (V) region of the γ chain is has a particular sequence which is known in the art as Vγ1, following the nomenclature of Tonegawa et al., for example), including the human equivalent thereof, which is believed to include Vδ1 and Vγ9 T cells. In one embodiment, γδ T cells having TCRs with Vδ1 are targeted by the method of the present method. These subsets of γδ T cells can be targeted, for example, by using an antibody that selectively binds to the Vγ1 chain of the TCR, for example.

In yet another preferred embodiment, T cells that are CD8+ (i.e., which express CD8) are preferred targets for the method of the present invention. Even more preferably, γδ T cells which express an αβ heterodimer of CD8 are preferably selectively targeted for depletion or inactivation according to the present method. CD8 is a costimulatory molecule expressed by subsets of both αβ T lymphocytes and γδ T lymphocytes. The CD8 molecule comprises two chains which can occur in the form of either a dimer of CD8α chains (i.e., a CD8 α homodimer) or a dimer of a CD8α chain and a CD8β chain (i.e., a CD8 αβ heterodimer). In αβ T cells, the CD8 molecule is typically expressed as a CD8 αβ heterodimer. In contrast, in γδ T cells, the CD8 molecule is typically expressed as a CD8 α homodimer, although the present inventors have found that Vγ4+ γδ T cells in the murine lung express CD8 as a CD8 αβ heterodimer. In acute AHR triggered by allergic inflammation, without being bound by theory, the present inventors believe that, even though it may be beneficial to maintain the Vγ4+ T cell population, it is preferable in the present method to deplete or inactivate the αβ T cell population. Therefore, in one aspect of the invention, T cells expressing CD8 β are targeted by the present method.

Antibodies against various T cell receptors useful in the present invention are known in the art. For example, antibodies against murine TCR-β, TCR-δ, and TCR-Vγ1 are described in the examples section. Antibodies against murine and human TCR-β, TCR-α, TCR-δ, TCR-γ, CD3, CD8 and CD4 are known in the art and are publicly available and referenced through Pharmingen (San Diego, Calif.), for example. Several of such antibodies are described in the Background section.

In one embodiment of the present method, a single antibody type is formulated for administration by aerosol delivery (i.e., the formulation contains antibodies of only one specificity). However, in another embodiment, the formulation contains at least two, and preferably three, four, five, or more different antibodies for aerosol delivery, wherein each antibody type selectively binds to a different receptor on a T cell, or to a different portion of the same receptor on a T cell. For example, in one aspect, the formulation contains antibodies against the γδ T cell antigen receptor and antibodies against the αβ T cell antigen receptor. In another aspect, the formulation contains antibodies against CD8 and antibodies against Vγ1 T cell antigen receptors. In another aspect, the formulation contains antibodies against the αβ T cell antigen receptor, antibodies against CD3, and antibodies against Vγ1 T cell antigen receptors. Any combination of such antibodies can be used and is contemplated by the present invention. The use of combinations of antibodies has the advantage of targeting more than one subset of T cells and may actually reduce the dosage of one type of antibody required to achieve a reduction in AHR. For example, by combining antibodies against TCR-β and TCR-Vγ1, one may be able to use less anti-TCR-β and still achieve the same effect with regard to AHR, thereby further decreasing the possibility that peripheral immune effects would be observed as a result of the treatment.

According to the present invention, "airway hyperresponsiveness" or "AHR" refers to an abnormality of the airways that allows them to narrow too easily and/or too much in response to a stimulus capable of inducing airflow limitation. AHR can be a functional alteration of the respiratory system resulting from inflammation in the airways or airway remodeling (e.g., such as by collagen deposition). Airflow limitation refers to narrowing of airways that can be irreversible or reversible. Airflow limitation or airway hyperresponsiveness can be caused by collagen deposition, bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and infiltrative diseases in and around the airways. Many of these causative factors can be associated with inflammation. AHR can be triggered in a patient with a condition associated with the above causative factors by exposure to a provoking agent or stimulus, also referred to herein as an AHR provoking stimulus. Such stimuli include, but are not limited to, an allergen, methacholine, a histamine, a leukotriene, saline, hyperventilation, exercise, sulfur dioxide, adenosine, propranolol, cold air, an antigen, bradykinin, acetylcholine, a prostaglandin, ozone, environmental air pollutants and mixtures thereof. The present invention is directed to airway hyperresponsiveness associated with any respiratory condition, and particularly, to allergen-induced airway hyperresponsiveness.

AHR can be measured by a stress test that comprises measuring a mammal's respiratory system function in response to a provoking agent (i.e., stimulus). AHR can be measured as a change in respiratory function from baseline plotted against the dose of a provoking agent (a procedure for such measurement and a mammal model useful therefore are described in detail below in the Examples). Respiratory function (and therefore the biological characteristics of AHR) can be measured by, for example, spirometry, plethysmograph, peak flows, symptom scores, physical signs (i.e., respiratory rate), wheezing, exercise tolerance, use of rescue medication (i.e., bronchodilators), cough and blood gases. In humans, spirometry can be used to gauge the change in respiratory function in conjunction with a provoking agent, such as methacholine or histamine. In humans, spirometry is performed by asking a person to take a deep breath and blow, as long, as hard and as fast as possible into a gauge that measures airflow and volume. The volume of air expired in the first second is known as forced expiratory volume ($FEV_1$) and the total amount of air expired is known as the forced vital capacity (FVC). In humans, normal predicted $FEV_1$ and FVC are available and standardized according to weight, height, sex and race. An individual free of disease has an $FEV_1$ and a FVC of at least about 80% of normal predicted values for a particular person and a ratio of $FEV_1$/FVC of at least about 80%. Values are determined before (i.e, representing a mammal's resting state) and after (i.e., representing a mammal's higher lung resistance state) inhalation of the provoking agent. The position of the resulting curve indicates the sensitivity of the airways to the provoking agent.

The effect of increasing doses or concentrations of the provoking agent on lung function is determined by measuring the forced expired volume in 1 second ($FEV_1$) and $FEV_1$ over forced vital capacity ($FEV_1$/FVC ratio) of the mammal challenged with the provoking agent. In humans, the dose or concentration of a provoking agent (i.e., methacholine or histamine) that causes a 20% fall in $FEV_1$ ($PC_{20}FEV_1$) is indicative of the degree of AHR. $FEV_1$ and FVC values can be measured using methods known to those of skill in the art.

Pulmonary function measurements of airway resistance ($R_L$) and dynamic compliance ($C_L$) and hyperresponsiveness can be determined by measuring transpulmonary pressure as the pressure difference between the airway opening and the body plethysmograph. Volume is the calibrated pressure change in the body plethysmograph and flow is the digital differentiation of the volume signal. Resistance ($R_L$) and compliance ($C_L$) are obtained using methods known to those of skill in the art (e.g., such as by using a recursive least squares solution of the equation of motion). The measurement of lung resistance ($R_L$) and dynamic compliance ($C_1$) are described in detail in the Examples. It should be noted that measuring the airway resistance ($R_L$) value in a non-human mammal (e.g., a mouse) can be used to diagnose airflow obstruction similar to measuring the $FEV_1$ and/or $FEV_1/FVC$ ratio in a human.

A variety of provoking agents are useful for measuring AHR values. Suitable provoking agents include direct and indirect stimuli, and are typically provoking agents that trigger AHR in vivo. As used herein, the phrase "provoking agent" can be used interchangeably with the phrase "AHR provoking stimulus". Preferred provoking agents or stimulus include, for example, an allergen, methacholine, a histamine, organic irritants, irritating gases and chemicals, a leukotriene, saline, hyperventilation, exercise, sulfur dioxide, adenosine, propranolol, cold air, an antigen, bradykinin, acetylcholine, a prostaglandin, ozone, environmental air pollutants and mixtures thereof. Preferably, for experimental induction of AHR, methacholine (Mch) is used as a provoking agent. Preferred concentrations of Mch to use in a concentration-response curve are between about 0.001 and about 100 milligram per milliliter (mg/ml). More preferred concentrations of Mch to use in a concentration-response curve are between about 0.01 and about 50 mg/ml. Even more preferred concentrations of Mch to use in a concentration-response curve are between about 0.02 and about 25 mg/ml. When Mch is used as a provoking agent, the degree of AHR is defined by the provocative concentration of Mch needed to cause a 20% drop of the $FEV_1$ of a mammal ($PC_{20methacholine}FEV_1$). For example, in humans and using standard protocols in the art, a normal person typically has a $PC_{20methacholine}FEV_1 > 8$ mg/ml of Mch. Thus, in humans, AHR is defined as $PC_{20methacholine}FEV_1 < 8$ mg/ml of Mch.

According to the present invention, respiratory function can also be evaluated with a variety of static tests that comprise measuring a mammal's respiratory system function in the absence of a provoking agent. Examples of static tests include, for example, spirometry, plethysmography, peak flows, symptom scores, physical signs (i.e., respiratory rate), wheezing, exercise tolerance, use of rescue medication (i.e., bronchodilators), blood gases and cough. Evaluating pulmonary function in static tests can be performed by measuring, for example, Total Lung Capacity (TLC), Thoracic Gas Volume (TgV), Functional Residual Capacity (FRC), Residual Volume (RV) and Specific Conductance (SGL) for lung volumes, Diffusing Capacity of the Lung for Carbon Monoxide (DLCO), arterial blood gases, including pH, $P_{O2}$ and $P_{CO2}$ for gas exchange. Both $FEV_1$ and $FEV_1/FVC$ can be used to measure airflow limitation. If spirometry is used in humans, the $FEV_1$ of an individual can be compared to the $FEV_1$ of predicted values. Predicted $FEV_1$ values are available for standard normograms based on the animal's age, sex, weight, height and race. A normal mammal typically has an $FEV_1$ at least about 80% of the predicted $FEV_1$ for the mammal. Airflow limitation results in a $FEV_1$ or FVC of less than 80% of predicted values. An alternative method to measure airflow limitation is based on the ratio of $FEV_1$ and FVC ($FEV_1/FVC$). Disease free individuals are defined as having a $FEV_1/FVC$ ratio of at least about 80%. Airflow obstruction causes the ratio of $FEV_1/FVC$ to fall to less than 80% of predicted values. Thus, a mammal having airflow limitation is defined by an $FEV_1/FVC$ less than about 80%.

As used herein, to reduce airway hyperresponsiveness refers to any measurable reduction in airway hyperresponsiveness and/or any reduction of the occurrence or frequency with which airway hyperresponsiveness occurs in a patient. A reduction in AHR can be measured using any of the above-described techniques or any other suitable method known in the art. Preferably, airway hyperresponsiveness, or the potential therefor, is reduced, optimally, to an extent that the mammal no longer suffers discomfort and/or altered function resulting from or associated with airway hyperresponsiveness. To prevent airway hyperresponsiveness refers to preventing or stopping the induction of airway hyperresponsiveness before biological characteristics of airway hyperresponsiveness as discussed herein can be substantially detected or measured in a patient. Once one or more of the biological characteristics of airway hyperresponsiveness can be substantially detected or measured, acute onset airway hyperresponsiveness is deemed to have occurred.

In one embodiment, the method of the present invention decreases methacholine responsiveness in the mammal. Preferably, the method of the present invention results in an improvement in a mammal's $PC_{20methacholine}FEV_1$ value such that the $PC_{20methacholine}FEV_1$ value obtained before use of the present method when the mammal is provoked with a first concentration of methacholine is the same as the $PC_{20methacholine}FEV_1$ value obtained after use of the present method when the mammal is provoked with double the amount of the first concentration of methacholine. Preferably, the method of the present invention results in an improvement in a mammal's $PC_{20methacholine}FEV_1$ value such that the $PC_{20methacholine}FEV_1$ value obtained before the use of the present method when the mammal is provoked with between about 0.01 mg/ml to about 8 mg/ml of methacholine is the same as the $PC_{20methacholine}FEV_1$ value obtained after the use of the present method when the mammal is provoked with between about 0.02 mg/ml to about 16 mg/ml of methacholine.

In another embodiment, the method of the present invention improves a mammal's $FEV_1$ by at least about 5%, and more preferably by between about 6% and about 100%, more preferably by between about 7% and about 100%, and even more preferably by between about 8% and about 100% of the mammal's predicted $FEV_1$. In another embodiment, the method of the present invention improves a mammal's $FEV_1$ by at least about 5%, and preferably, at least about 10%, and even more preferably, at least about 25%, and even more preferably, at least about 50%, and even more preferably, at least about 75%.

In yet another embodiment, the method of the present invention results in an increase in the $PC_{20methacholine}FEV_1$ of a mammal by about one doubling concentration towards the $PC_{20methacholineFEV1}$ of a normal mammal. A normal mammal refers to a mammal known not to suffer from or be susceptible to abnormal AHR. A patient, or test mammal refers to a mammal suspected of suffering from or being susceptible to abnormal AHR.

Therefore, a mammal that has airway hyperresponsiveness is a mammal in which airway hyperresponsiveness can be measured or detected, such as by using one of the above methods for measuring airway hyperresponsiveness, wherein the airway hyperresponsiveness is typically induced by exposure to an AHR provoking stimulus, as described above. Similarly, a mammal that has allergen-induced airway hyperresponsiveness is a mammal in which airway hyperresponsiveness can be measured or detected, such as by using one of the above methods for measuring airway hyperresponsiveness, wherein the airway hyperresponsiveness is induced by exposure to an allergen. To be induced by an AHR provoking stimulus, such as an allergen, the airway hyperresponsiveness is apparently or obviously, directly or indirectly triggered by (e.g., caused by, a symptom of, indicative of, concurrent with) an exposure to the stimulus. Symptoms, or biological characteristics, of AHR include, but are not limited to, indicators of altered respiratory function (described in detail above), change in respiratory rate, wheezing, lowered exercise tolerance, cough and altered blood gases. Detection or measurement of any one or more of such symptoms is indicative of the onset of acute AHR.

In the case of an allergen, the airway hyperresponsiveness is apparently or obviously, directly or indirectly triggered by an allergen to which a mammal has previously been sensitized. Sensitization to an allergen refers to being previously exposed one or more times to an allergen such that an immune response is developed against the allergen. Responses associated with an allergic reaction (e.g., histamine release, rhinitis, edema, vasodilation, bronchial constriction, airway inflammation), typically do not occur when a naive individual is exposed to the allergen for the first time, but once a cellular and humoral immune response is produced against the allergen, the individual is "sensitized" to the allergen. Allergic reactions then occur when the sensitized individual is re-exposed to the same allergen (e.g., an allergen challenge). Once an individual is sensitized to an allergen, the allergic reactions can become worse with each subsequent exposure to the allergen, because each re-exposure not only produces allergic symptoms, but further increases the level of antibody produced against the allergen and the level of T cell response against the allergen.

Typically, conditions associated with allergic responses to antigens (i.e., allergens) are at least partially characterized by inflammation of pulmonary tissues. Such conditions or diseases are discussed above. It is noted that the present invention is specifically directed to the treatment of AHR, and as such, it is not required that the condition or causative factor that caused the AHR, such as allergic inflammation, be significantly reduced or "cured", although the effects of the present method likely extend to inhibition of allergic inflammation. The method of the present invention is fully effective to reduce AHR even after the inflammatory response in the lungs of the mammal is fully established. A mammal that is at risk of developing airway hyperresponsiveness is a mammal that has been exposed to, or is at risk of being exposed to, an AHR provoking stimulus that is sufficient to trigger AHR, but does not yet display a measurable or detectable characteristic or symptom of airway hyperresponsiveness, such symptoms being described previously herein. A mammal that is at risk of developing allergen-induced airway hyperresponsiveness is a mammal that has been previously sensitized to an allergen, and that has been exposed to, or is at risk of being exposed to, an amount of the allergen that is sufficient to trigger AHR (i.e., a triggering, or challenge dose of allergen), but does not yet display a measurable or detectable characteristic or symptom of airway hyperresponsiveness. A mammal that is at risk of developing airway hyperresponsiveness also includes a mammal that is identified as being predisposed to or susceptible to such a condition or disease.

Inflammation is typically characterized by the release of inflammatory mediators (e.g., cytokines or chemokines) which recruit cells involved in inflammation to a tissue. A condition or disease associated with allergic inflammation is a condition or disease in which the elicitation of one type of immune response (e.g., a Th2-type immune response) against a sensitizing agent, such as an allergen, can result in the release of inflammatory mediators that recruit cells involved in inflammation in a mammal, the presence of which can lead to tissue damage and sometimes death. Airway hyperresponsiveness can occur in a patient that has, or is at risk of developing, any chronic obstructive disease of the airways, including, but not limited to, asthma, chronic obstructive pulmonary disease, allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, and parasitic lung disease. The method of the present invention is particularly useful for treating allergen-induced airway hyperresponsiveness, and most particularly, allergen-induced asthma, in addition to other forms of airway hyperresponsiveness, lung cancer, and idiopathic pulmonary disease.

The effectiveness of the present method is typically measured or evaluated by measuring the decrease or inhibition of AHR in the patient, as described in detail above. In some scenarios, one may wish to additionally observe the effect on the T cell number or function in the patient, and particularly in the pulmonary tissues of the patient. For example, the clinician can perform a lavage on the lung tissue of the patient and measure T cell numbers and/or activation. A decrease in the number of T cells as compared to a prior number of T cells is typically evaluated by measuring proliferation of T cells, for example, by using a standard T cell proliferation assay (e.g., uptake of $[^3H]$-thymidine). T cell proliferation assays are well known in the art. Other methods for determining a change in the number of T cells can be evaluated by detecting or measuring the expression level, and/or the distribution of $\alpha$-chain, $\beta$-chain, $\gamma$-chain and/or $\delta$ chain usage in the receptors of a population of $\alpha\beta$ or $\gamma\delta$ T cells and determining whether there is a change in the expression level and/or distribution of one or more T cell receptor types in the population. Such assays, including both molecular and flow cytometric methods, and the reagents (e.g., antibodies, hybridization probes and PCR primers specific for various TCR chains) for performing such assays, are known in the art.

Events associated with T cell activation or biological activity include, but are not limited to, T cell proliferation, cytokine production (e.g., interleukin-2 (IL-2), IL-4, IL-5, IL-10, interferon-$\gamma$ (IFN-$\gamma$), tumor necrosis factor-$\alpha$ (TNF-$\alpha$)), upregulation of cytokine receptors (e.g., IL-2 receptor, TNF-$\alpha$ receptor), calcium mobilization, upregulation of cell surface molecules associated with T cell activation (e.g., CD44, CD69), upregulation of expression and activity of signal transduction proteins associated with T cell activation, chemokine production, altered T cell migration, accumulation of T cells at specific tissue sites and/or cytoskeletal reorganization. In the method of the present invention, one may wish to look for a reduction in any of the above-characteristics of T cell activation in the pulmonary tissue of the patient that is treated as a marker of the efficacy of the treatment. Methods of measuring these activation events are well known in the art. For example, after a T cell has been stimulated with an antigenic or mitogenic stimulus, characteristics of T cell activation can be determined by a method including, but not limited to: measuring cytokine production by the T cell (e.g., by immunoassay or biological assay); measuring intracellular and/or extracellular calcium mobilization (e.g., by calcium mobilization assays); measuring T cell proliferation (e.g., by proliferation assays such as radioisotope incorporation); measuring upregulation of cytokine receptors on the T cell surface, including IL-2R (e.g., by flow cytometry, immunofluorescence assays, immunoblots, RNA assays); measuring upregulation of other receptors associated with T cell activation on the T cell surface (e.g., by flow cytometry, immunofluorescence assays, immunoblots, RNA assays); measuring reorganization of the cytoskeleton (e.g., by immunofluorescence assays, immunoprecipitation, immunoblots); measuring upregulation of expression and activity of signal transduction proteins associated with T cell activation (e.g., by kinase assays, phosphorylation assays, immunoblots, RNA assays); and, measuring specific effector functions of the T cell (e.g., by proliferation assays).

As discussed above, the method of the present invention includes the use of an antibody or antigen binding fragment that selectively binds to a receptor on a T cell which, by causing apoptosis of the T cell or otherwise targeting the T cell for depletion from the pulmonary tissues, reduces airway hyperresponsiveness in the patient. Preferred antibody specificities and sources of publicly available antibodies have been discussed in detail previously herein. According to the present invention, antibodies are characterized in that they comprise immunoglobulin domains and as such, they are members of the immunoglobulin superfamily of proteins. Generally speaking, an antibody molecule comprises two types of chains. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to a L chain by a disulfide bond. There are only two types of L chains referred to as lambda ($\lambda$) and kappa ($\kappa$) chains. In contrast, there are five major H chain classes referred to as isotypes. The five classes include immunoglobulin M (IgM or $\mu$), immunoglobulin D (IgD or $\delta$), immunoglobulin G (IgG or $\lambda$), immunoglobulin A (IgA or $\alpha$), and immunoglobulin E (IgE or $\epsilon$). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 ($\gamma$1), IgG2 ($\gamma$2), IgG3 ($\gamma$3) and IgG4 ($\gamma$4), and two subclasses of IgA including IgA1 ($\alpha$1) and IgA2 ($\alpha$2).

Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete $C_H$ domain comprises three sub-domains (CH1, CH2, CH3) and a hinge region. Together, one H chain and one L chain can form an arm of an immunoglobulin molecule having an immunoglobulin variable region. A complete immunoglobulin molecule comprises two associated (e.g., di-sulfide linked) arms. Thus, each arm of a whole immunoglobulin comprises a $V_{H+L}$ region, and a CH+L region. As used herein, the term "variable region" or "V region" refers to a $V_{H+L}$ region (also known as an Fv fragment), a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease may produce two fragments. An antigen binding fragment is referred to as an Fab, an Fab', or an F(ab')$_2$ fragment. A fragment lacking the ability to bind to antigen is referred to as an Fc fragment. An Fab fragment comprises one arm of an immunoglobulin molecule containing a L chain ($V_L$+$C_L$ domains) paired with the $V_H$ region and a portion of the $C_H$ region (CH1 domain). An Fab' fragment corresponds to an Fab fragment with part of the hinge region attached to the CH1 domain. An F(ab')$_2$ fragment corresponds to two Fab' fragments that are normally covalently linked to each other through a di-sulfide bond, typically in the hinge regions.

The $C_H$ domain defines the isotype of an immunoglobulin and confers different functional characteristics depending upon the isotype. For example, $\mu$ constant regions enable the formation of pentameric aggregates of IgM molecules and a constant regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding sites. Thus, the hypervariable loops determine the specificity of an immunoglobulin and are termed complementarity-determining regions (CDRS) because their surfaces are complementary to antigens.

Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. Each H and L chain CDR region is flanked by FW regions.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity which refers to the sum total of the strength with which an immunoglobulin binds to an antigen. Immunoglobulin binding affinity can be measured using techniques standard in the art, such as competitive binding techniques, equilibrium dialysis or BIAcore methods. As used herein, valency refers to the number of different antigen binding sites per immunoglobulin molecule (i.e., the number of antigen binding sites per antibody molecule of antigen binding fragment). For example, a monovalent immunoglobulin molecule can only bind to one antigen at one time, whereas a bivalent immunoglobulin molecule can bind to two or more antigens at one time, and so forth. Both monovalent and bivalent antibodies that selectively bind to T cell receptors are encompassed herein.

In one embodiment of the present invention, a monovalent antibody can be used as a regulatory compound (discussed below). Such an antibody is not capable of aggregating receptors. Divalent antibodies can also be used in the present invention. Particularly preferred antibodies are monovalent or divalent antibodies that are capable of causing the T cell to which the antibody binds to be destroyed or removed from the pulmonary tissues.

In one embodiment, the antibody is a bi- or multi-specific antibody. A bi-specific (or multi-specific) antibody is capable of binding two (or more) antigens, as with a divalent (or multivalent) antibody, but in this case, the antigens are different antigens (i.e., the antibody exhibits dual or greater specificity). A bi-specific antibody suitable for use in the present method includes an antibody having: (a) a first portion (e.g., a first antigen binding portion) which binds to a receptor on a T cell; and (b) a second portion which binds to another cell surface molecule, including another receptor expressed by the T cell. For example, the second portion can be capable of targeting the regulatory antibody to a specific target cell (i.e., the regulatory antibody binds to a target molecule).

In one embodiment, antibodies of the present invention that are particularly useful in human patients are humanized antibodies. Humanized antibodies are molecules having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains. Humanized antibodies can be produced, for example, by modeling the antibody variable domains, and producing the antibodies using genetic engineering techniques, such as CDR grafting (described below). A description various techniques for the production of humanized antibodies is found, for example, in Morrison et al. (1984) *Proc. Natl. Acad. Sci. USA* 81:6851-55; Whittle et al. (1987) *Prot. Eng.* 1:499-505; Co et al. (1990) *J. Immunol.* 148:1149-1154; Co et al. (1992) *Proc. Natl. Acad. Sci. USA* 88:2869-2873; Carter et al. (1992) *Proc. Natl. Acad. Sci.* 89:4285-4289; Routledge et al. (1991) *Eur. J. Immunol.* 21:2717-2725 and PCT Patent Publication Nos. WO 91/09967; WO 91/09968 and WO 92/113831. Humanized antibodies against TCR-β chains are described in U.S. Pat. No. 5,861,155, incorporated herein by reference in its entirety.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

A preferred method to produce antibodies of the present invention includes (a) administering to an animal an effective amount of a protein or peptide (e.g., a TCR protein or peptide) to produce the antibodies and (b) recovering the antibodies. In another method, antibodies of the present invention are produced recombinantly. For example, once a cell line, for example a hybridoma, expressing an antibody according to the invention has been obtained, it is possible to clone therefrom the cDNA and to identify the variable region genes encoding the desired antibody, including the sequences encoding the CDRs. From here, antibodies and antigen binding fragments according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts, e.g. members of the genera Pichia, Saccharomyces, or Kluyveromyces,) and mammalian cell lines, e.g. a non-producing myeloma cell line, such as a mouse NSO line, or CHO cells. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (PNAS 74, 5463, (1977)) and the Amersham International plc sequencing handbook; and site directed mutagenesis can be carried out according to the method of Kramer et al. (*Nucl. Acids Res.* 12, 9441, (1984)) and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in the aforementioned European Patent Applications.

Alternative methods, employing, for example, phage display technology (see for example U.S. Pat. No. 5,969,108, U.S. Pat. No. 5,565,332, U.S. Pat. No. 5,871,907, U.S. Pat. No. 5,858,657) or the selected lymphocyte antibody method of U.S. Pat. No. 5,627,052 may also be used for the production of antibodies and/or antigen fragments of the invention, as will be readily apparent to the skilled individual.

The invention also extends to non-antibody polypeptides, sometimes referred to as binding partners, that have been designed to bind selectively to and cause the depletion of a T cell according to the present invention. Examples of the design of such polypeptides, which possess a prescribed ligand specificity are given in Beste et al. (*Proc. Natl. Acad. Sci.* 96:1898-1903, 1999), incorporated herein by reference in its entirety.

Typically, an antibody useful in the present method is administered in a formulation suitable for aerosol delivery, also referred to herein as an aerosolized antibody formulation. Such a formulation generally includes a carrier, and preferably, a pharmaceutically acceptable carrier. According to the present invention, a "pharmaceutically acceptable carrier" includes pharmaceutically acceptable excipients and/or pharmaceutically acceptable delivery vehicles, which are suitable for use in the aerosol administration of the formulation to a suitable in vivo site. A suitable in vivo site is preferably a T cell that expresses the receptor against which the antibody is directed. Preferred pharmaceutically acceptable carriers are capable of maintaining the antibody in a form that, upon arrival of the antibody at the cell target in a patient, the antibody is capable of selectively binding to the receptor, resulting in the depletion of the T cell that expresses such receptor.

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Formulations of the present invention can be sterilized by conventional methods and/or lyophilized.

One type of pharmaceutically acceptable carrier includes a controlled release formulation that is capable of slowly releasing a formulation of the present invention into the lungs of a patient. As used herein, a controlled release formulation comprises an antibody of the present invention in a controlled release vehicle. Suitable controlled release vehicles include, but are not limited to, biocompatible polymers, other polymeric matrices, microcapsules, microparticles, liposomes, or lipospheres.

Other suitable carriers include any carrier that can be bound to or incorporated with the antibody that extends that half-life of the antibody to be delivered. Such a carrier can include any suitable protein carrier or even a fusion segment that extends the half-life of an antibody when delivered in vivo.

Preferred carriers of the present invention include, any carrier that is suitable for use in an aerosol delivery route according to the present invention. Such carriers include, but are not limited to: dry, dispersible powders; small capsules (e.g., microcapsules or microparticles); liposomes; and nebulized sprays. Dry, dispersible powders suitable for aerosolized delivery of antibodies are described in detail in U.S. Pat. No. 6,165,463, incorporated herein by reference in its entirety (See also products from Inhale Therapeutic Systems, Inc. and Quadrant Technology). Suitable liposomes for use with the present invention include any liposome, and particularly, any liposome that is sufficiently small to be delivered by aerosol in the method of the invention. Microcapsules and microparticles are known in the art. For example, Alliance Pharmaceutical Corporation has a particle engineering technology, called PulmoSphere, prepared by a proprietary spray-drying process and are designed to be both hollow and porous. A product by Ventolin consists of micronized albuterol (free base) particles suspended in a mixture of CFC-based propellants. Proventil HFA contains micronized albuterol sulfate and a small percentage of an ethanol co-solvent to solubilize the stabilizing oleic acid surfactant. Incorporation of drugs into liposomes has several advantages for aerosol delivery. Because liposomes are relatively insoluble, the retention time of some drugs in the lung can be prolonged for increased efficacy. Liposomes are also taken up primarily by phagocytic cells which make them particularly suitable for delivery of certain drugs. Nebulized formulations are described in the Examples. Devices for delivery of aerosolized formulations include, but are not limited to, pressurized metered dose inhalers (MDI), dry powder inhalers (DPI), and metered solution devices (MSI), and include devices that are nebulizers and inhalers.

According to the method of the present invention, an effective amount of an antibody that inhibits AHR to administer to a mammal comprises an amount that is capable of reducing airway hyperresponsiveness (AHR) without being toxic to the mammal. An amount that is toxic to a mammal comprises any amount that causes damage to the structure or function of a mammal (i.e., poisonous).

In one embodiment the aerosolized antibody formulation of the present invention is administered to the patient in conjunction with another agent that supports the treatment of AHR. Such agents can include, but are not limited to: corticosteroids, (oral, inhaled and injected), β-agonists (long or short acting), leukotriene modifiers (inhibitors or receptor antagonists), antihistamines, phosphodiesterase inhibitors, sodium cromoglycate, nedocrimal, and theophylline.

In one embodiment, the effectiveness of an AHR inhibiting antibody to protect a mammal from AHR in a mammal having or at risk of developing AHR can be measured in doubling amounts. For example, the ability of a mammal to be protected from AHR (i.e., experience a reduction in or a prevention of) by administration of a given antibody is significant if the mammal's $PC_{20methacholine}FEV_1$ is at 1 mg/ml before administration of the antibody and is at 2 mg/ml of Mch after administration of the antibody. Similarly, an antibody is considered effective if the mammal's $PC_{20methacholine}FEV_1$ is at 2 mg/ml before administration of the antibody and is at 4 mg/ml of Mch after administration of the antibody. A preferred effective amount of an antibody comprises an amount that is capable of increasing the $PC_{20methacholine}FEV_1$ of a mammal treated with the antibody by about one doubling concentration towards the $PC_{20methacholine}FEV_1$ of a normal mammal. A normal mammal refers to a mammal known not to suffer from or be susceptible to abnormal AHR. A test mammal refers to a mammal suspected of suffering from or being susceptible to abnormal AHR.

In one embodiment of the present invention, in a mammal that has AHR, an effective amount of an antibody to administer to a mammal is an amount that measurably reduces AHR in the mammal as compared to prior to administration of the antibody. In another embodiment, an effective amount of an antibody to administer to a mammal is an amount that measurably reduces AHR in the mammal as compared to a level of airway AHR in a population of mammals with inflammation that is associated with AHR wherein the antibody was not administered. The antibody that binds to a receptor on a T cell according to the present invention is preferably capable of reducing AHR in a mammal, even when the antibody is administered after the onset of the physical symptoms of AHR (i.e., after acute onset AHR). Most preferably, an effective amount of the antibody is an amount that reduces the symptoms of AHR to the point where AHR is no longer detected in the patient. In another embodiment, an effective amount of the antibody is an amount that prevents, or substantially inhibits the onset of AHR when the antibody is administered prior to exposure of the patient to an AHR provoking stimulus, such as an allergen, in a manner sufficient to induce AHR in the absence of the antibody.

In another embodiment, an effective amount of an antibody according to the method of the present invention, comprises an amount that results in an improvement in a mammal's $PC_{20methacholine}FEV_1$ value such that the $PC_{20methacholine}FEV_1$ value obtained before administration of the antibody when the mammal is provoked with a first concentration of methacholine is the same as the $PC_{20methacholine}FEV_1$ value obtained after administration of the antibody when the mammal is provoked with double the amount of the first concentration of methacholine. A preferred amount of an antibody comprises an amount that results in an improvement in a mammal's $PC_{20methacholine}FEV_1$ value such that the $PC_{20methacholine}FEV_1$ value obtained before administration of the antibody is between about 0.01 mg/ml to about 8 mg/ml of methacholine is the same as the $PC_{20methacholine}FEV_1$ value obtained after administration of the antibody is between about 0.02 mg/ml to about 16 mg/ml of methacholine.

As previously described herein, the effectiveness of an antibody to protect a mammal having or susceptible to AHR can be determined by measuring the percent improvement in $FEV_1$ and/or the $FEV_1/FVC$ ratio before and after administration of the antibody. In one embodiment, an effective amount of an antibody comprises an amount that is capable of reducing the airflow limitation of a mammal such that the $FEV_1/FVC$ value of the mammal is at least about 80%. In another embodiment, an effective amount of an antibody comprises an amount that is capable of reducing the airflow limitation of a mammal such that the $FEV_1/FVC$ value of the mammal is improved by at least about 5%, or at least about 100 cc or PGFRG 10L/min. In another embodiment, an effective amount of an antibody comprises an amount that improves a mammal's $FEV_1$ by at least about 5%, and more preferably by between about 6% and about 100%, more preferably by between about 7% and about 100%, and even more preferably by between about 8% and about 100% (or about 200 ml) of the mammal's predicted $FEV_1$. In another embodiment, an effective amount of an antibody comprises an amount that improves a mammal's $FEV_1$ by at least about 5%, and preferably, at least about 10%, and even more preferably, at least about 25%, and even more preferably, at least about 50%, and even more preferably, at least about 75%.

It is within the scope of the present invention that a static test can be performed before or after administration of a provocative agent used in a stress test. Static tests have been discussed in detail above.

A suitable single dose of an antibody of the present invention to administer to a mammal is a dose that is capable of reducing or preventing airway hyperresponsiveness in a mammal when administered one or more times over a suitable time period. In particular, a suitable single dose of an antibody comprises a dose that improves AHR by a doubling dose of a provoking agent or improves the static respiratory function of a mammal.

To estimate the dosage, it is first noted that, in the examples presented herein, the present inventors have demonstrated (e.g., see FIG. 1) that an aerosolized antibody formulation of the present invention, delivered by nebulization, can be administered at a concentration of as little as 5 µg/ml of antibody, and still cause a reduction in AHR in the mammal. In practice, using the method of delivery in the examples, one places 8-10 subject mice into the nebulizer, wherein the mice are exposed to approximately 10 mls of nebulized formulation (i.e., approximately 1 ml per mouse) containing, for example, 10 µg/ml of antibody. Therefore, much of the 10 mls of formulation does not enter the airways of the mouse and instead condenses on the wall of the chamber. Indeed, the amount of ovalbumin entering the airways of the mice in such a system has been experimentally estimated to be a minute fraction of the actual amount nebulized into the chamber. Even assuming that each mouse receives approximately 1 ml of the aerosolized formulation into the airways (i.e., ~10 µg antibody per mouse in this example), this equates to ~400 µg×kilogram$^{-1}$ body weight of the mouse (assuming a mouse body weight of ~25 g), not taking into account the alometric scaling method described below. In reality, and without being bound by theory, the present inventors believe that the actual amount delivered to each mouse is on the order of 100 to 1000-fold less, and indeed, in humans, it known in the art that, using conventional methods for aerosol delivery, only about 10% of the delivered solution typically enters the deep airways, even using an inhaler. If the aerosolized delivery is by direct inhalation, one may assume a dosage of about 10% of that administered by nebulization methods. Finally, one of skill in the art will readily be capable of converting a mouse dosage to a human dosage using alometric scaling. Essentially, a scale of dosage from mouse to human is based on the clearance ratio of a compound and the body surface of the mouse. The conversion for mg/kg is 1/12th of the "no observed adverse event level" (NOEL) to obtain the concentration for human dosage. This calculation assumes that the elimination between mouse and human is the same, which is believed to be the case for antibodies.

Accordingly, a preferred single dose of an antibody comprises between about 1 ng×kilogram$^{-1}$ and about less than 1 mg×kilogram$^{-1}$ body weight of a mammal. A more preferred single dose of an antibody comprises between about 20 ng×kilogram$^{-1}$ and about 600 µg×kilograms$^{-1}$ body weight of the mammal.

An even more preferred single dose of an antibody, particularly when the antibody formulation is delivered by nebulization, comprises between about 20 ng×kilogram$^{-1}$ and about 600 µg×kilograms$^{-1}$ body weight of the mammal, and more preferably, between about 20 ng×kilogram$^{-1}$ and about 500 µg×kilogram$^{-}$, and more preferably, between about 20 ng×kilograms$^{-1}$ and about 400 µg×kilograms$^{-1}$, and more preferably, between about 20 ng×kilogram$^{-1}$ and about 300 µg×kilogram$^{-1}$, and more preferably, between about 20 ng×kilogram$^{-1}$ and about 200 µg×kilograms$^{-1}$, and more preferably, between about 20 ng×kilogram$^{-1}$ and about 100 µg×kilogram$^{-1}$, and more preferably, between about 20 ng×kilogram$^{-1}$ and about 50 µg×kilograms$^{\times 1}$ body weight of the mammal.

Another preferred single dose of an antibody, particularly when the antibody formulation is delivered by nebulization, comprises between about 200 ng×kilograms$^{-1}$ and about 600 µg×kilogram$^{-1}$ body weight of the mammal, and more preferably, between about 200 ng×kilogram$^{-1}$ and about 500 µg×kilogram$^{-1}$, and more preferably, between about 200 ng×kilogram$^{-1}$ and about 400 µg×kilogram$^{-1}$, and more preferably, between about 200 ng×kilograms$^{-1}$ and about 300 µg×kilogram$^{-1}$, and more preferably, between about 200 ng×kilogram$^{-1}$ and about 200 µg×kilogram$^{-1}$, and more preferably, between about 200 ng×kilogram$^{-1}$ and about 100 µg×kilogram$^{-1}$, and more preferably, between about 200 ng×kilogram$^{-1}$ and about 50 µg×kilogram$^{-1}$ body weight of the mammal.

Another preferred single dose of an antibody, particularly when the antibody formulation is delivered by direct inhalation from an inhaler, comprises between about 2 ng×kilogram$^{-1}$ and about 100 µg×kilogram$^{-1}$ body weight of the mammal, and more preferably, between about 2 ng×kilogram$^{-1}$ and about 50 µg×kilogram$^{-1}$, and more preferably, between about 2 ng×kilogram$^{-1}$ and about 10 µg×kilogram$^{-1}$, and more preferably, between about 2 ng×kilogram$^{-1}$ and about 5 µg×kilogram$^{-1}$, and more preferably, between about 2 ng×kilogram$^{-1}$ and about 1 µg×kilogram$^{-1}$, and more preferably, between about 2 ng×kilogram$^{-1}$ and about 0.5 µg×kilogram$^{-1}$, and more preferably, between about 2 ng×kilogram$^{-1}$ and about 0.25 µg×kilogram$^{-1}$, and more preferably, between about 2 ng×kilograms$^{-1}$ and about 0.1 µg×kilogram$^{-1}$ body weight of the mammal.

In another embodiment, the antibody is administered at a dose of less than about 500 µg antibody per milliliter of formulation, and preferably, less than about 250 µg antibody per milliliter of formulation, and more preferably, less than about 100 µg antibody per milliliter of formulation, and more preferably, less than about 50 µg antibody per milliliter of formulation, and more preferably, less than about 40 µg antibody per milliliter of formulation, and more preferably, less than about 30 µg antibody per milliliter of formulation, and more preferably, less than about 20 µg antibody per milliliter of formulation, and more preferably, less than about 10 µg antibody per milliliter of formulation, and even more preferably, between about 5 µg antibody and about 10 µg antibody per milliliter of formulation.

One of skill in the art will be able to determine that the number of doses of an antibody to be administered to a mammal is dependent upon the extent of the airway hyperresponsiveness and the underlying condition of which AHR is a symptom, and the response of an individual patient to the treatment. In addition, the clinician will be able to determine the appropriate timing for delivery of the agent in a manner effective to reduce AHR in the mammal. Preferably, the antibody is delivered within 48 hours prior to exposure of the patient to an amount of an AHR provoking stimulus effective to induce AHR, and more preferably, within 36 hours, and more preferably within 24 hours, and more preferably within 12 hours, and more preferably within 6 hours, 5 hours, 4 hours, 3 hours, 2 hours, or 1 hour prior to exposure of the patient to an amount of AHR provoking stimulus effective to induce AHR. In one embodiment, the antibody is administered as soon as it is recognized 5 (i.e., immediately) by the patient or clinician that the patient has been exposed or is about to be exposed to an AHR provoking stimulus, and especially an AHR provoking stimulus to which the patient is sensitized (i.e., an allergen). In another embodiment, the antibody is administered upon the first sign of development of AHR (i.e., acute onset AHR), and preferably, within at least 2 hours of the development of symptoms of AHR, and more preferably, within at least 1 hour, and more preferably within at least 30 minutes, and more preferably within at least 10 minutes, and more preferably within at least 5 minutes of development of symptoms of AHR. Symptoms of AHR and methods for measuring or detecting such symptoms have been described in detail above. Preferably, such administrations are given until signs of reduction of AHR appear, and then as needed until the symptoms of AHR are gone.

The method of the present invention can be used in any animal, and particularly, in any animal of the Vertebrate class, Mammalia, including, without limitation, primates, rodents, livestock and domestic pets. Preferred mammals to treat using the method of the present invention include humans.

Aerosol (inhalation) delivery can be performed using methods standard in the art (see, for example, Stribling et al., *Proc. Natl. Acad. Sci. USA* 189:11277-11281, 1992, which is incorporated herein by reference in its entirety). Carriers suitable for aerosol delivery are described above. Devices for delivery of aerosolized formulations include, but are not limited to, pressurized metered dose inhalers (MDI), dry powder inhalers (DPI), and metered solution devices (MSI), and include devices that are nebulizers and inhalers. The following websites also contain information regarding current pulmonary delivery devices and carriers: http://www.iddc.org/iddc.htm and http://members.tripod.com/Chaubal/pulmonary.html.

Also included as an embodiment of the present invention are any of the aerosolized antibody formulations described herein, including antibodies of a single specificity or combinations of antibodies as disclosed herein, and formulated in the dosages specified herein, for use in the treatment of airway hyperresponsiveness. In one embodiment, such formulations include at least one additional agent that is useful for the treatment of AHR, as described above.

The following examples are provided for the purposes of illustration and are not intended to limit the scope of the present invention.

EXAMPLES

Example 1

The following example describes the comparison of aerosolized versus intravenously given mAbs against TCR-β in ovalbumin (OVA) sensitized and challenged mice.

The classical animal model of allergic inflammation (see, e.g., Takeda et al., (1997). *J. Exp. Med.* 186, 449-454; Renz et al., 1992, *J. Allergy Clin. Immunol.* 89:1127-1138; Larsen et al., 1992, *J. Clin. Invest.* 89:747-752; and Saloga et al., 1993, *J. Clin. Invest.* 91:133-141) was used to assess the ability of aerosolized mAbs to influence AHR. The present inventors and others have previously shown that αβ T cells are necessary for the development of allergic inflammation and airway hyperresponsiveness (AHR) (Holt, *J. Exp. Med.* 183:1297-1301 (1996); Lahn et al., *Nature Med.* 5:1150-6 (1999)). In this experiment, C57BL/6 mice were injected twice with Alum/OVA intraperitoneally (sensitization) before a three day exposure to aerosolized OVA (challenge). The exact procedure has been previously published (Lahn et al., *Nature Med.* 5:1150-6 (1999)), and is referred to herein as the 2ip3N protocol. It should be noted that both immunization and subsequent antigen (OVA) challenge are required to observe antigen-specific T cell responses in mice and to study AHR as a result of acute allergic inflammation. A protocol referred to herein as the "3N protocol" involves suboptimal sensitzation to ovalbumin by 3 aerosolized exposures to OVA in the absence of the initial systemic sensitization. This protocol is useful for studying AHR in the absence of an allergic inflammation. The 2ip3N protocol, therefore, offers a model for studying allergic inflammation, while the 3N protocol can be used to study non-specific stimuli that can precipitate AHR that is not dependent on previously sensitized $\alpha\beta$ T cells.

In brief, for the 2ip3N protocol, mice were sensitized by intraperitoneal injection of 20 µg of ovalbumin (Grade V, Sigma) emulsified in 2.25 mg alum (Alum® Inject; Pierce, Rockford, Ill.) in a total volume of 100 µl on days 0 and 14. On days 28, 29 and 30, mice were challenged via the airways by a 20-minute inhalation exposure to aerosols of ovalbumin (1% in saline) obtained from a DeVilbiss ultrasonic nebulizer (particle size 1-5 µm). Age-matched, control animal groups consisted of mice that were injected with alum alone (non-sensitized) and then exposed either to aerosols of saline or to aerosolized ovalbumin, and mice sensitized to ovalbumin but subsequently exposed to aerosols of saline.

Airway responsiveness was assessed as a change in airway function after challenge with aerosolized methacholine (MCh) via the airways. Anesthetized, tracheostomized mice were mechanically ventilated and lung function was assessed as a modification to previously described procedures (Lahn et al., Nature Med. 5:1150-6 (1999); Martin et al., *J. Appl. Physiol.* 64:2318-2323 (1988); Takeda et al., *J. Exp. Med.* 186: 449-454(1997)). A four-way connector was attached to the tracheostomy tube (stainless steel cannula, 18G), with two ports connected to the inspiratory and expiratory sides of two ventilators. Ventilation was achieved at 160 breaths per minute and a tidal volume of 0.15 ml with a positive end-expiratory pressure of 2-4 cm $H_2O$ (Harvard Apparatus, South Natwick, Mass.). Aerosolized MCh was administered for 10 breaths at a rate of 60 breaths/min in increasing concentrations (6.25, 12.5, 25, 50, 100 mg/ml MCh) with a tidal volume of 0.5 ml by the second ventilator (Shinano Manufacturing Co., Tokyo, Japan). The Plexiglas chamber containing the mouse was continuous with a 1.0-liter glass bottle filled with copper gauze to stabilize the volume signal for thermal drift. Transpulmonary pressure was detected by a pressure transducer with one side connected to the fourth port of a four-way connector and the other side connected to a second port on the plethysmograph. Changes in lung volume were measured by detecting pressure changes in the plethysmographic chamber through a port in the connecting tube with a pressure transducer and then referenced to a second copper-gauze filled 1.0-liter glass bottle. Flow was measured by digital differentiation of the volume signal. Lung resistance ($R_L$) and dynamic compliance ($C_{dyn}$) were continuously computed (Labview, National Instruments, TX) by fitting flow, volume, and pressure to an equation of motion. After each aerosol MCh challenge, the data were continuously collected for 1 to 5 minutes and maximum values of $R_L$ and minimum values of $C_{dyn}$ were taken to express changes in murine airway function. Baseline and saline controls were all similar among all examined mice and results were reported as percentages of saline control.

Figure 1B:
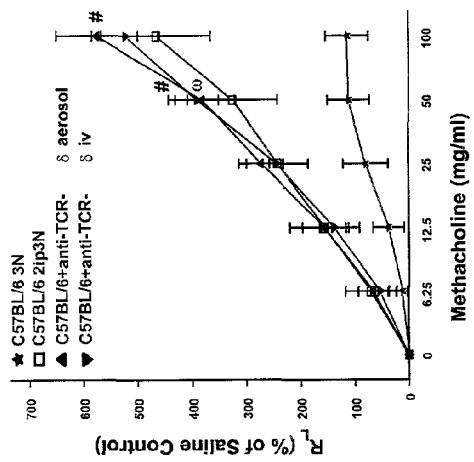
Figure 1D:
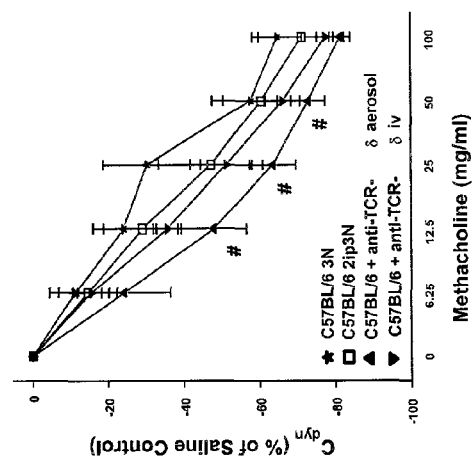

In comparison to mice receiving only the three day aerosol with OVA, referred to herein as the 3N protocol (★ in FIGS. 1A and B), sensitized and challenged mice, referred to herein as mice receiving the 2ip3N protocol (□ in FIGS. 1A and B), showed a marked increase in airway resistance ($R_L$; FIG. 1A) and compliance ($C_{dyn}$; FIG. 1B). As expected, sensitized and challenged C57BL/6 mice that were injected intravenously (i.v.) with 200 µg of mAb against TCR-β (clone H57-597) 10 days prior to the three day OVA aerosol exposure showed a significant decrease in AHR (● in FIGS. 1A and B; p<0.05) The significant differences between 2ip3N alone and 2ip3N with i.v. H57 are indicated by a in FIG. 1A. Depletion of the respective αβ T cell population in the lung was confirmed by flowcytometry.

Surprisingly, adding 10 µg/ml of the mAb H57 on the last of the three-day OVA exposures led to a similar decrease of AHR as the i.v. injection of the same mAb (■ in FIGS. 1A and B). The significant differences between 2ip3N and 2ip3N with aerosol H57 are indicated by * in FIG. 1A. A titration of the mAb suggested that a minimum of 5 µg/ml are necessary to obtain the reduction of AHR as shown.

Example 2

The following example describes the comparison of aerosolized versus intravenously given mAbs against TCR-δ in ovalbumin (OVA) sensitized and challenged mice.

In this example, experiments were conducted as described in Example 1, but with the use of a mAb against TCR-δ (a 1:1 mixture of mAbs GL3 (Goodman et al., *J. Exp. Med.* 170: 1569 (1989)) and 403A10 Itohara et al., *Proc. Natl. Acad. Sci. USA* 86:5094-5098 (1989)). As previously published (Lahn et al., *Nature Med.* 5:1150-6 (1999)), the intravenous injection of mAbs against TCR-δ (▼ in FIGS. 1C and 1D) caused only a slight increase in AHR when compared to 2ip3N treated C57BL/6 mice in the absence of antibody (□ in FIGS. 1C and 1D). The significant differences between 2ip3N treated mice and 2ip3N mice treated with i.v. anti-TCR-δ are shown by "ω" in FIG. 1C. Again, the addition of 10 µg/ml of anti-TCR-δ to the last OVA aerosol application (▲ in FIGS. 1C and 1D) had a similar effect as the intravenous injection of the same mAb. The significant differences between 2ip3N treated mice and 2ip3N treated mice with i.v. anti-TCR-δ are shown by # in FIGS. 1C and 1D. This experiment serves also as a control to the injection with H57 (Example 1), because the mAbs against TCR-δ are of the same mammal specificity as the H57 (i.e. Armenian hamster IgG).

Example 3

The following example describes the comparison of aerosolized mAbs against TCR-Vγ1 and TCR-Vγ4 in ovalbumin (OVA) sensitized and challenged mice.

Finally, the γδ T cell subsets Vγ1 and Vγ4 were examined for their contribution to the regulation of AHR. Experiments were performed as described in Examples 1 and 2 above, but with the use of mAbs against γδ TCR subsets having Vγ1 or Vγ4.

Figure 1E:
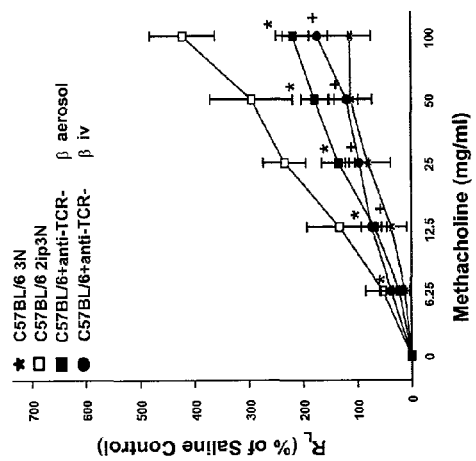
FIGS. 1E and 1F show the airway resistance ($R_L$) (FIG. 1E) and dynamic compliance ($C_{dyn}$) (FIG. 1F) for mice receiving anti-TCR-Vγ4 and anti-TCRVγ1 by aerosol delivery.
Figure 1F:
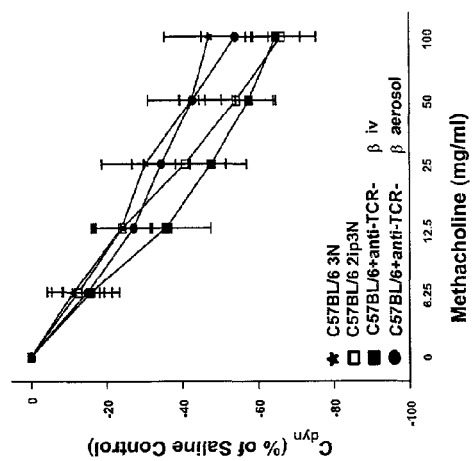

The aerosol application of mAbs against Vγ1 showed a significant reduction in AHR of 2ip3N treated C57BL/6 mice (top ▶ in FIGS. 1E and 1F). The significant differences between 2ip3N treated mice and 2ip3N treated mice with aerosol anti-Vγ1 are indicated by "τ" in FIGS. 1E and 1F). This result indicates that the removal of this particular subset of γδ T cells, which may be recruited during allergic inflammation to the lung, has a beneficial effect on regulating AHR associated with allergic inflammation. Thus, an aerosol of a particular subset of γδ T cells in humans, presumably the Vγ9 subset or a recruited/expanded Vδ1 subset, could offer a new therapeutic treatment option.

Interestingly, the application of anti-Vγ4 worsened the AHR response particularly in the compliance (bottom ) in FIG. 1F), suggesting that this subset is important for the smaller airway regulation.

Example 4

The following example describes the cellular composition in bronchoalveolar lavage (BAL) fluid of 2ip3N treated C57BL/6 mice after treatment with mAbs.

In this experiment, C57BL/6 mice were treated using the 3N or 2ip3N protocols, as described in Example 1. Some groups were treated with intravenous or aerosolized mAb against TCR-β (H57), TCR-δ, TCR-Vγ1 or TCR-Vγ4. Following assessment of airway function, the lungs were lavaged once with 1 ml of sterile Hank's balanced salt solution (HBSS) pre-warmed at 37° C. The recovered BAL fluids were placed in Eppendorf tubes and were centrifuged at 4° C. for 5 min at 1,500 rpm. The obtained cell pellets were resuspended in 200 μl of sterile phosphate-buffered saline (PBS) and total cell numbers were determined from counting of crystal violet-stained aliquots using a hemacytometer. Differential cell counts were determined from cytospin preparations stained with Leukostat (Fisher Diagnostics, Pittsburgh, Pa.). At least 200 cells were counted from each slide in a blinded fashion.

Figure 2A:
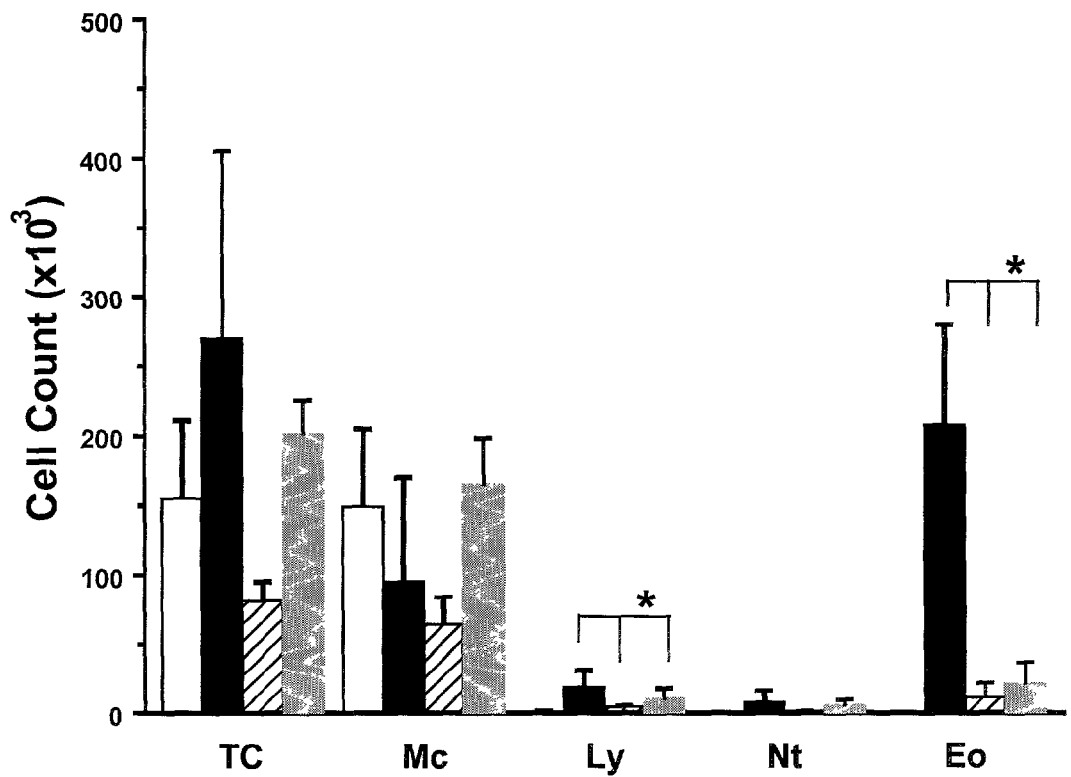
FIG. 2A shows the effect on BAL fluid cell composition in mice treated with mAb against TCR-β.

FIG. 2A shows the effect of treatment of mice with mAb against TCR-β. The open bars represent C57BL/6 mice treated with the 3N protocol alone, solid black bars are 2ip3N treated mice, hatched bars show mice treated with intravenously injected H57 (anti-TCR-β), and gray solid bars indicate mice treated with aerosolized H57. The BAL Fluid cell composition includes total cell counts (TC), macrophages (Mc), lymphocytes (Ly), neutrophils (Nt) and eosinophils (Eo). Significant differences are indicated by ✱(p<0.05).

The results show that both intravenous injection and aerosol application of anti-TCR-β(H57) have a similar profound effect on suppressing eosinophil counts in the BAL fluid. Preliminary studies of the lung tissue has revealed that the Vγ1 T cell subset is increased about 2-3 fold under allergic conditions (e.g., the 2ip3N protocol), as compared to non-allergic conditions (e.g., the 3N protocol).

Figure 2B:
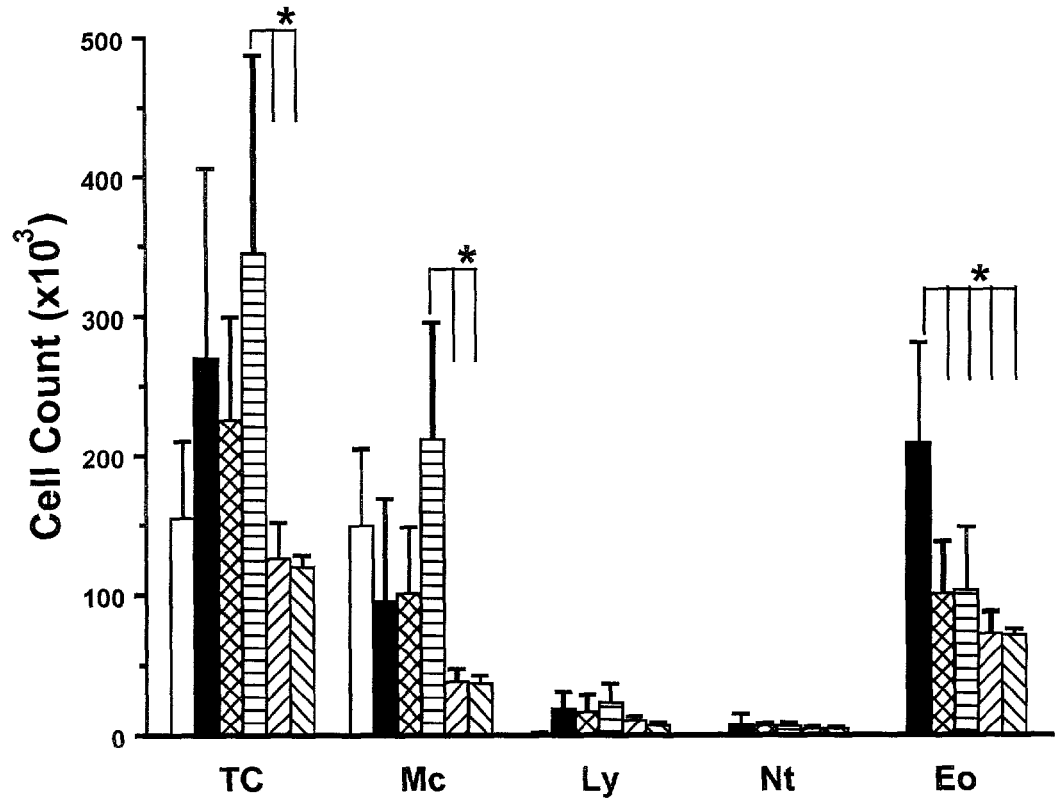
FIG. 2B shows the effect on BAL fluid cell composition in mice treated with mAb against TCR-δ, TCR-Vγ1, and TCR-Vγ4.

FIG. 2B shows the effect of treatment with mAbs against TCR-δ, TCR-Vγ1 and TCR-Vγ4. Open bars represent 3N treated C57BL/6 mice, solid black bars represent 2ip3N treated C57BL/6 mice, cross-hatched bars represent intravenous anti-TCR-δ treated mice, horizontal-hatched bars represent aerosol anti-TCR-δ treated mice, left-hatched bars represent aerosol anti-TCR-Vγ1 treated mice, and right-hatched bars represent aerosol anti-TCR-Vγ4 treated mice. The BAL Fluid cell composition includes total cell counts (TC), macrophages (Mc), lymphocytes (Ly), neutrophils (Nt) and eosinophils (Eo). Significant differences are indicated by ✱(p<0.05). Surprisingly, aerosolized mAbs against both γδ T cell subsets (i.e., Vγ1 and Vγ4) lead to a suppression of eosinophils in the BAL fluid, indicating that each may function as an eosinophil attractant, although each subset has a different function in terms of regulating AHR.

Example 5

The following example confirms that airway responsiveness is regulated by pulmonary γδ T cells, and shows that aerosolized mAb deplete pulmonary T cells, but have no significant effect on peripheral T cells.

In this experiment, aerosolized anti-TCR mAbs were used to target pulmonary γδ T cells directly, rather than by systemic administration. Mice (C57BL/6 from The Jackson Laboratory, Bar Harbor, Me.) were treated using the 3N protocol for airway hyperresponsiveness. Briefly, mice received the following treatments: (1) airway exposure to nebulized OVA (1% in saline) alone, using ultrasonic nebulization for 20 min on three consecutive days (i.e., the 3N protocol); (2) airway exposure to nebulized OVA on three consecutive days (3N protocol) with the addition of 10 μg/ml of the designated mAb to aerosol solution on the third exposure day (see below); (3) intravenous injection of mAbs as previously described (Lahn et al., *Nature Med.* 5:1150-6 (1999)). Airway responsiveness was assessed 48 hours following the last nebulized OVA exposure for all 3N treated mice as described in Example 1. For each of these treatments, groups of at least 4 mice of each type were analyzed in every independent experiment.

For antibody administration, systemic depletion of γδ T cells and subsets was accomplished with mAb as previously described (Lahn et al., *Nature Med.* 5:1150-6 (1999)) and used to determine the quality of mAbs for depletion and usage as aerosols. For intravenous administration, 200 μg of mAbs against TCR-δ (a 1:1 mixture of mAbs GL3 (Goodman et al., *J. Exp. Med.* 170:1569 (1989) (Pharmingen) and 403A10 (Itohara et al., *Proc. Natl. Acad. Sci. USA* 86:5094-5098 (1989)) or TCR-β (H57-597; Pharmingen) were injected into the tail vein of a mouse. Mice were then exposed to 3N treatment three days later and after a total of 7 days, depletion of pulmonary and splenic γδ T cells was assessed at the time of airway function measurements. On the third and last day of the 3N treatment, indicated mAbs were added to the OVA solution and airway responsiveness assessed 48 hrs later as described in Example 1. The success of this treatment was assessed by staining for CD3$^+$TCR-δ$^+$ or CD3$^+$TCR-β$^+$ T cells following lung digestion and T cell enrichment using nylon-wool columns. Purity of CD3$^+$ cells after nylon-wool enrichment was 70-80%.

Figure 3A:
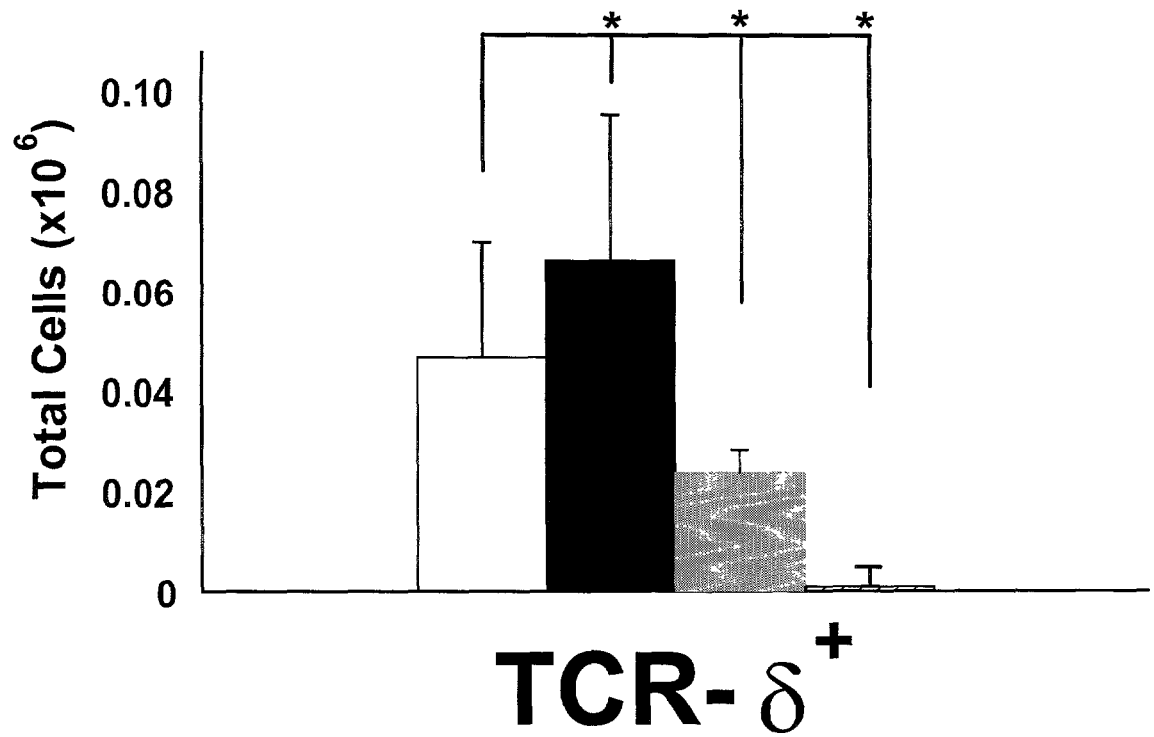
FIGS. 3A and 3B show the total cell counts for γδ pulmonary T lymphocytes (FIG. 3A) and splenic T lymphocytes (FIG. 3B) in mice treated anti-TCR-δ using the suboptimal method of airway sensitization.
Figure 3B:
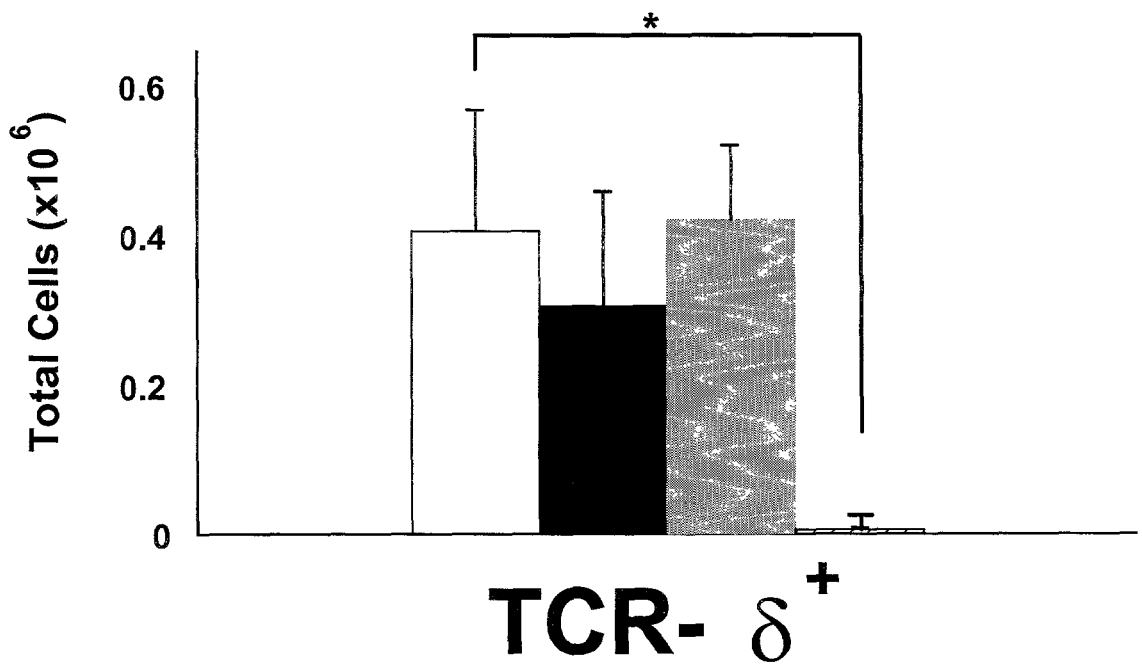

FIGS. 3A and 3B show the total cell counts for γδ cells after nylon-wool enrichment of pulmonary lymphocytes (FIG. 3A) and of splenic lymphocytes (FIG. 3B): C57BL/6 no treatment is shown by open bars; C57BL/6 3N treatment is shown by black bars; C57BL/6+anti-TCR-δ aerosol after 48 hours is shown by gray bars; and C57BL/6+anti-TCR-δ i.v. is shown by hatched bars. Each bar represents data from at least three independent experiments using a total of 9-12 mice. Significant differences (p<0.05) are indicated by *. In this experiment, treatment with aerosolized mAb against the δ chain (10 μg/ml anti-TCR-δ mAb) reduced pulmonary γδ T cells (FIG. 3A), but had no discernible effect on splenic γδ T cells, both at 48 hrs (FIG. 3B) and one week after the last OVA aerosol exposure (not shown). As expected, the systemic antibody treatment by intravenous injection of anti-TCR-δ mAbs depleted pulmonary as well as splenic γδ T cells (FIGS. 3A and 3B). Thus, the aerosolized mabs preferentially targeted pulmonary γδ T cells.

Depletion of γδ T cells in OVA-challenged C57BL/6 mice resulted in increased lung resistance ($R_L$) and decreased dynamic compliance ($C_{dyn}$) in response to inhaled MCh (data not shown). Treatment with aerosolized anti-TCR-β mAb had no effect in this 3N protocol (data not shown). Treatment with aerosolized anti-TCR-δ mAbs administered only 48 hrs prior to MCh provocation elicited similar or larger changes in airway responsiveness as did the systemic administration of the mAb, even though the antibody dose necessary to achieve the same effect was much smaller. Moreover, systemic treatment required more time (about 1 week) to take effect (data not shown).

Example 6

The following example compares the roles of Vγ4+ T cells and Vγ1+ T cells in the 3N protocol of airway responsiveness.

In normal C57BL/6 mice, the retrievable pulmonary γδ T cell population consisted of about $5\times10^4$ lymphocytes. At 48 hrs following the airway challenges with OVA (3N protocol), only minor increases in total γδ T cell numbers were detected. The majority of these cells express Vγ6 at the mRNA level (Sim et al., *Int. Immunol.* 6:1287-95 (1994)), although antibodies for the specific detection of such cells are not yet available. About ⅓ expressed Vγ4 (about $1.5\times10^4$) and even fewer expressed Vγ1 (about $0.7\times10^4$). First, mice that are genetically deficient in the two major pulmonary γδ T cells subsets, Vγ6+ and Vγ4+ T cells (Sunaga et al., *J. Immunol.* 158:4223-4228 (1997)) were examined. TCR-Vγ4/6$^{-/-}$mice were back-crossed to a C57BL/6 background and were used after five back-crosses (TCR-Vγ4/6$^{-/-}$ were a kind gift from K. Ikuta (Sunaga et al., *J. Immunol.* 158:4223-4228 (1997))). In comparison with either C57BL/6 mice or their littermates of similar genetic background, the genetically deficient mice showed increased airway responsiveness following airway challenge with OVA under the 3N protocol (FIG. 4A & 4B), consistent with a negative regulatory function of either one or of both of the deficient γδ T cell subsets, but not of Vγ1+ T cells.

Next, available Vγ-specific mAbs and the aerosolized antibody-treatment 3N protocol were used to assess and compare functional roles of the Vγ1+ pulmonary subset (using mAb 2.11; (Pereira et al., *J. Exp. Med.* 182:1921-1930 (1995))) and the Vγ4+ pulmonary subset (using mAb UC3-10A6; Pharmingen) in normal C57BL/6 mice. Treatment with anti-TCR-Vγ4 mAb resulted in increased airway responsiveness (FIG. 4C & 4D) using the 3N protocol, equivalent to the increases obtained with either aerosolized or systemic pan-specific anti-TCR-δ mAbs, or those observed in genetically γδ T cell-deficient mice (Lahn et al., *Nature Med.* 5:1150-6 (1999)). In contrast, anti-TCR-Vγ1 mAb had no effect in this 3N protocol (FIG. 4C & 4D), although this antibody efficiently depletes Vγ1+ T cells as was previously demonstrated (Huber et al., *J Immunol* 165:4174-81 (2000)) and its depletion/inactivation inhibits AHR in allergen sensitized and challenged (i.e., 2ip3N treated) mice, as demonstrated in Example 3.

Because of the present inventors earlier findings that γδ T cell-dependent negative regulation of airway responsiveness targets an αβ T cell-independent mechanism of airway stimulation (Lahn et al., *Nature Med.* 5:1150-6 (1999)), it was determined whether the regulator population of pulmonary Vγ4+ T cells also shared this independence from αβ T cells. Using B6.TCR-β$^{-/-}$ mice (Taconic (Germantown, N.Y.)) instead of C57BL/6 mice, this was found to be the case (FIGS. 4E & 4F). Moreover, this result confirmed the distinctive role of Vγ4+ T cells as negative regulators of airway responsiveness (i.e., inhibitors of AHR). B6.TCR-β$^{-/-}$ mice not only harbor more pulmonary γδ T cells than C57BL/6 mice, but also the relative sizes of the pulmonary subsets are skewed such that Vγ1+ T cells emerge as the predominant population (data not shown). Despite this difference, there was no indication that Vγ1+ T cells contributed to the negative regulation of airway responsiveness in these mice.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to reduce airway hyperresponsiveness in a mammal that has, or is at risk of developing, airway hyperresponsiveness, comprising administering to the lungs of said mammal an aerosolized antibody formulation comprising antibodies that selectively bind to a receptor on a T cell selected from the group consisting of: a T cell antigen receptor (TCR) selected from the group consisting of an αβ TCR and a γδ TCR, CD3, CD4 and CD8, wherein the binding of the antibodies to the receptor causes the depletion or inactivation of the T cell, wherein administration of the antibody formulation reduces airway hyperresponsiveness in said mammal;

wherein said aerosolized antibody formulation is administered at a dose of less than about 1 μg×kilogram$^{-1}$ body weight of said mammal; and wherein the administration of the aerosolized antibody formulation affects pulmonary T cell responses in the mammal, while peripheral T cell responses in the mammal are neither substantially stimulated nor substantially inhibited.

2. The method of claim 1, wherein said aerosolized antibody formulation is administered at a dose of less than about 0.5 μg×kilogram$^{-1}$ body weight of said mammal.

3. The method of claim 1, wherein said aerosolized antibody formulation is administered at a dose of less than about 0.1 μg×kilogram$^{-1}$ body weight of said mammal.

4. The method of claim 1, wherein said aerosolized antibody formulation is administered at a dose of less than about 20 ng×kilogram$^{-1}$ body weight of said mammal.

\* \* \* \* \*